US009597417B2

(12) United States Patent
Polli et al.

(10) Patent No.: US 9,597,417 B2
(45) Date of Patent: Mar. 21, 2017

(54) COMPOSITIONS AND METHODS TO EVALUATE HEPATOBILIARY/GASTROINTESTINAL HEALTH, ENTEROHEPATIC CIRCULATION, AND DRUG INTERACTIONS

(71) Applicants: The United States of America as represented by the Department of Veteran Affairs, Washington, DC (US); UNIVERSITY OF MARYLAND, BALTIMORE, Baltimore, MD (US)

(72) Inventors: James E. Polli, Ellicott City, MD (US); Jean-Pierre Raufman, Baltimore, MD (US); Diana Vivian, Arnold, MD (US)

(73) Assignee: THE UNITED STATES OF AMERICA AS REPRESENTED BY THE DEPARTMETN OF VETERANS AFFAIRS, Washington, DC (US)

( * ) Notice: Subject to any disclaimer, the term of this patent is extended or adjusted under 35 U.S.C. 154(b) by 123 days.

(21) Appl. No.: 14/535,397

(22) Filed: Nov. 7, 2014

(65) Prior Publication Data
US 2015/0132228 A1 May 14, 2015

Related U.S. Application Data

(60) Provisional application No. 61/901,819, filed on Nov. 8, 2013.

(51) Int. Cl.
A61K 49/08 (2006.01)
A61K 31/56 (2006.01)
A61K 49/10 (2006.01)

(52) U.S. Cl.
CPC ............ A61K 49/085 (2013.01); A61K 49/10 (2013.01)

(58) Field of Classification Search
CPC ......... A61K 31/56; A61K 31/58; A61K 49/00
See application file for complete search history.

(56) References Cited

PUBLICATIONS

Diana Vivian et al., Design and Characterization of a Novel Fluorinated Magnetic Resonance Imaging Agent for Functional Analysis of Bile Acid Transporter Activity, Pharm Res. 2013, 30, 1240-1251.*
Priya Vijayyvargiya et al. Diagnostic Mehtods for Bile Acid Mealabsorption in Clinical Practice, Clin Gastroenterol Hepatol, 2013, 11(10), 1232-1239.*
Altschul, S.F. et al. (1990) Basic local alignment search tool. J Mol Biol 215:403-410.
Balakrishnan, A. et al. (2005) Deleterious effect of high transporter expression in the estimation of transporter kinetics. AAPS J 7:R6224.
Balakrishnan, A. et al. (2005) Development of stably transfected monolayer overexpressing the human apical sodium-dependent bile acid transporter (hASBT). Pharm Res 22:1269-1280.
Balakrishnan, A. et al. (2007) Bias in estimation of transporter kinetic parameters from overexpression systems: Interplay of transporter expression level and substrate affinity. J Pharmacol Exp Ther 320:133-144.
Batta, A.K. et al. (1984) Substrate specificity of cholylglycine hydrolase for the hydrolysis of bile acid conjugates. J Biol Chem 259:15035-15039.
Brydon, W.G. et al. (1996) Serum 7 alpha-hydroxy-4-cholesten-3-one and selenohomocholyltaurine (SeHCAT) whole body retention in the assessment of bile acid induced diarrhoea. Eur J Gastroenterol Hepatol 8:117-123.
Chen, X. et al. (2006) Transactivation of rat apical sodium-dependent bile acid transporter and increased bile acid transport by 1alpha,25-dihydroxyvitamin D3 via the vitamin D receptor. Mol Pharmacol 69:1913-1923.
Dawson, P.A. et al. (2003) Targeted deletion of the ileal bile acid transporter eliminates enterohepatic cycling of bile acids in mice. J Biol Chem 278:33920-33927.
Dawson, P.A. (2011) Role of the intestinal bile acid transporters in bile acid and drug disposition. Handb Exp Pharmacol 201:169-203.
Frisch, K. et al. (2012) [N-methyl-11C]cholylsarcosine, a novel bile acid tracer for PET/CT of hepatic excretory function: radiosynthesis and proof-of-concept studies in pigs. J Nucl Med 53:772-778.
Heydorn, S. et al. (1999) Bile acid replacement therapy with cholylsarcosine for short-bowel syndrome. Scand J Gastroenterol 34:818-823.
Hofmann, A.F. et al. (1983) Description and simulation of a physiological pharmacokinetic model for the metabolism and enterohepatic circulation of bile acids in man. Cholic acid in healthy man. J Clin Invest 71:1003-1022.
Hofmann, A.F. et al. (2009) Chronic diarrhea due to excessive bile acid synthesis and not defective ileal transport: A new syndrome of defective FGF19 release. Clin Gastroenterol Hepatol 7:1151-1154.
Huijghebaert, S.M. et al. (1986) Influence of the amino acid moiety on deconjugation of bile acid amidates by cholylglycine hydrolase or human fecal cultures. J Lipid Res 27:742-752.
Jiang, Z.X. et al. (2009) Symmetry-guided design and fluorous synthesis of a stable and rapidly excreted imaging tracer for ($^{19}$)F MRI. Angew Chem Int Ed Engl 48:4755-4758.
Khalid, U. et al. (2010) Bile acid malabsorption: a forgotten diagnosis? Clin Med 10:124-126.
Kolhatkar, V. et al. (2012) Structural requirements of bile acid transporters: C-3 and C-7 modifications of steroidal hydroxyl groups. Eur J Pharm Sci 46:86-99.
Lenicek, M. et al. (2011) Bile acid malabsorption in inflammatory bowel disease: Assessment by serum markers. Inflamm Bowel Dis 17:1322-1327.
Leonhardt, M. et al. (2010) Hepatic uptake of the magnetic resonance imaging contrast agent Gd-EOB-DTPA: role of human organic anion transporters. Drug Metab Dispos 38:1024-8.

(Continued)

Primary Examiner — Michael G Hartley
Assistant Examiner — Jagadishwar Samala
(74) Attorney, Agent, or Firm — Marianne Fuierer; Moore & Van Allen, PLLC

(57) ABSTRACT

The present invention relates to the synthesis and use of a novel trifluorinated bile acid analog, that being, CA-sar-TFMA which is useful as an imaging probe, diagnostic agent or contrast agent and is resistant to bacterial deconjugation, wherein the trifluorinated bile acid analog can be used as a $^{19}$F MRI tracer exhibiting an increased half-life due to its resistance to choloylglycine hydrolase.

22 Claims, 9 Drawing Sheets

(56) References Cited

PUBLICATIONS

Li, F. et al. (2007) Dynamic NMR study and theoretical calculations on the conformational exchange of valsartan and related compounds. *Magn Reson Chem* 45:929-936.

Lillienau, J. et al. (1992) Physicochemical and physiological properties of cholylsarcosine. A potential replacement detergent for bile acid deficiency states in the small intestine. *J Clin Invest* 89:420-31.

Lorenzo-Zúñiga, V. et al. (2003). Oral bile acids reduce bacterial overgrowth, bacterial translocation, and endotoxemia in cirrhotic rats. *Hepatology*. 37:551-557.

Merrick, M.V. et al. (1982) Enterohepatic circulation in man of a gamma-emitting bile-acid conjugate, 23-Selena-25-Homotaurocholic Acid (SeHCAT). *J Nucl Med* 23:126-130.

Pedersen, L. et al. (1973) Rapid screening of increased bile acid deconjugation and bile acid malabsorption by means of the glycine-1-(14 C) cholylglycine assay. *Scand J Gastroenterol* 8:665-672.

Schmassmann, A. et al. (1990) Transport, metabolism, and effect of chronic feeding of cholylsarcosine, a conjugated bile acid resistant to deconjugation and dehydroxylation. *Gastroenterology* 98:163-174.

Schmassmann, A. et al. (1993) Cholylsarcosine, a new bile acid analogue: metabolism and effect on biliary secretion in humans. *Gastroenterology* 104:1171-81.

Sciarretta, G. et al. (1987) 75Se HCAT test in the detection of bile acid malabsorption in functional diarrhoea and its correlation with small bowel transit. *Gut* 28:970-975.

Smith, M.J. et al. (2000) Bile acid malabsorption in persistent diarrhoea. *J R Coll Physicians* Lond 34:448-451.

Srinivas, M. et al. (2007) Fluorine-19 MRI for visualization and quantification of cell migration in a diabetes model. *Magn Reson Med* 58:725-734.

Swaan, P.W. et al. (1997) Molecular modeling of the intestinal bile acid carrier: a comparative molecular field analysis study. *J Comput Aided Mol Des*.:11:581-588.

Vertzoni, M. et al. (2004) Dissolution media simulating the intralumenal composition of the small intestine: physiological issues and practical aspects. *J Pharm Pharmacol* 56:453-462.

Vertzoni, M. et al. (2008) Determination of intralumenal individual bile acids by HPLC with charged aerosol detection. *J Lipid Res* 49:2690-2695.

Vijayvargiya, P. et al. (2013) Methods for diagnosis of bile acid malabsorption in clinical practice. *Clin Gastroenterol Hepatol* 11:1232-1239.

Vivian, D. et al. (2013) Design and characterization of a novel fluorinated magnetic resonance imaging agent for functional analysis of bile acid transporter activity. *Pharm Res* 30:1240-1251.

Vivian, D. et al. (2014) In vivo performance of a novel fluorinated magnetic resonance imaging agent for functional analysis of bile acid transport. *Mol Pharm* 11, 1575-1582.

Wedlake, L. et al. (2009) Systematic review: the prevalence of idiopathic bile acid malabsorption (I-BAM) as diagnosed by SeHCAT scanning in patients with diarrhoea-predominant irritable bowel syndrome (IBS). *Aliment Pharmacol Ther* 30:707-717.

Wedlake, L. et al. (2009) Effectiveness and tolerability of colesevelam hydrochloride for bile-acid malabsorption in patients with cancer: a retrospective chart review and patient questionnaire. *Clin Ther* 31:2549-2558.

Williams, A.J. et al. (1991) Idiopathic bile acid malabsorption—a review of clinical presentation, diagnosis, and response to treatment. *Gut* 32:1004-1006.

Yu, J.X. et al. (2005) $^{19}$F: A Versatile Reporter for Non-Invasive Physiology and Pharmacology Using Magnetic Resonance. *Curr Med Chem* 12:819-848.

Zheng, X. et al. (2010) Identification of Inhibitor Concentrations to Efficiently Screen and Measure Inhibition Ki Values against Solute Carrier Transporters. *Eur J Pharm Sci* 41:43-52.

* cited by examiner

COMPOSITIONS AND METHODS TO EVALUATE HEPATOBILIARY/GASTROINTESTINAL HEALTH, ENTEROHEPATIC CIRCULATION, AND DRUG INTERACTIONS

CROSS REFERENCE TO RELATED APPLICATION

The present application claims priority to U.S. Provisional Patent Application No. 61/901,819 filed on Nov. 8, 2013, the contents of which are herein incorporated by reference herein for all purposes.

STATEMENT OF FEDERAL SUPPORT

This invention was made with government support under Grant No. FD-U-004320 awarded by the Food and Drug Administration, and Grant Nos. DK067872 and DK093406 awarded by the National Institutes of Health. The government has certain rights in the invention.

BACKGROUND OF THE INVENTION

Field of the Invention

The present invention relates to detection probes and methods of use, and more particularly, related to $^{19}$F-labeled bile acid tracer and methods of use to evaluate hepatobiliary and/or gastrointestinal health, enterohepatic circulation, and/or drug interactions.

Description of the Related Art

Bile acids are produced in the liver as end products of cholesterol metabolism. After their synthesis, bile acids are conjugated to glycine or taurine, and secreted into bile by the bile salt export pump (BSEP; ABCB11) and to a lesser extent by the multidrug resistance associated protein 2 (MRP2; ABCC2). Between meals, bile is stored in the gallbladder. In response to a meal, the gallbladder contracts and bile acids are emptied into the duodenum where they increase lipid solubility through micelle formation. Bile acids are passively absorbed throughout the small intestine, as well as actively absorbed by enterocytes in the terminal ileum via the apical sodium-dependent bile acid transporter (ASBT, SLC10A2). After uptake by enterocytes, bile acids are effluxed into the portal circulation by the organic solute transporters (OSTα-OSTβ; SLC51A, SLC51B) and to a lesser extent by multidrug resistance protein 3 (MRP3; ABCC3). At the liver, the bile acids are taken up by hepatocytes via the Na$^+$/taurocholate cotransporting polypeptide (NTCP, SLC10A1) and the organic anion transporting polypeptides (OATPs) for re-secretion into bile. This enterohepatic circulation of bile acids maintains the human bile acid pool between 2-4 g. Bile acids circulate several times daily with less than 10% lost in feces.[1,2]

Excess bile acids entering the colon contribute to the symptoms of bile acid malabsorption (BAM) which is characterized by excess fecal bile acids and chronic watery diarrhea and is often misdiagnosed as diarrhea-predominant irritable bowel syndrome (IBS-D).[3] BAM is considered responsible for 30-50% of unexplained chronic diarrhea.[4,5,6,7] Although BAM can be attributed to ileal resection/damage or rare ASBT mutations, the cause of most cases of idiopathic BAM is unknown. Recent advances in understanding this disease suggest that overproduction of bile acids resulting from deficient fibroblast growth factor (FGF)-19 may be a common feature of BAM.[8] FGF19 is part of the mechanism for feedback inhibition of hepatic bile acid synthesis from cholesterol, and regulation of bile acid synthesis is impaired in its absence. This dysregulation leads to hepatic overproduction of bile acids, exceeding the ileal absorptive capacity, thereby increasing colonic exposure and diarrhea.

In the United States, diagnosis of BAM is limited by the lack of sensitive, specific and cost-effective tests. $^{75}$Se-homocholic acid-taurine (HCAT), a $^{75}$Se-labeled gamma-emitting synthetic bile acid used to measure intestinal uptake of bile acids, is available for use in selected European countries, but has not been approved by the FDA.[9] Diagnostic criteria for this test are based on the percentage of $^{75}$Se-HCAT retained in the body one week after oral administration. Other methods to diagnose BAM include $^{14}$C-taurocholate stool measurement[10], 7α-hydroxy-4-cholesten-3-one serum measurement as a biomarker of bile acid formation[11], and blood FGF19 measurement[12] (inversely related to 7α-hydroxy-4-cholesten-3-one levels). However, these methods are time-consuming, difficult, not readily available, or not validated clinically. Hence, BAM is often diagnosed by administering bile acid sequestrants, such as colesevelam, in a therapeutic trial[13,14], an approach that is not FDA-approved for this indication, lacks specificity and has a high rate of false-negative diagnosis.[7]

To address these limitations, CA-lys-TFA, a conjugate of trifluoroacetyl-lysine and cholic acid, was previously synthesized and tested for the diagnosis of BAM by using in vivo imaging of the trifluorinated bile acid analogue with $^{19}$F magnetic resonance imaging (MRI).[15] The CA-lys-TFA was used as a tagged bile for tracking to determine its accumulation in the gallbladder to determine the differentiation between normal and impaired bile acid transport. However, when CA-lys-TFA was used as an imaging agent, it was susceptible to bacterial metabolism, that being, removal of its amino acid side chain by choloylglycine hydrolase (CGH), a bacterial bile acid deconjugating enzyme located predominantly in the colon and in smaller amounts in the terminal ileum.[15]

Thus, it would be advantageous to provide an imaging probe having the ability to non-invasively assess bile acid transport and diagnose impaired intestinal bile acid uptake, such as BAM, while not being susceptible to bacterial deconjugation by CGH.

SUMMARY OF THE INVENTION

The present invention relates to the synthesis and use of a novel trifluorinated bile acid analogue useful as an imaging probe, diagnostic agent, contrast agent and is resistant to bacterial deconjugation, wherein the trifluorinated bile acid analogue can be used as a $^{19}$F MRI tracer exhibiting an increase half-life due to the resistance to CGH.

In one aspect the present invention provides for a trifluorinated bile acid analogue, that being, CA-sar-TFMA, having the following structure:

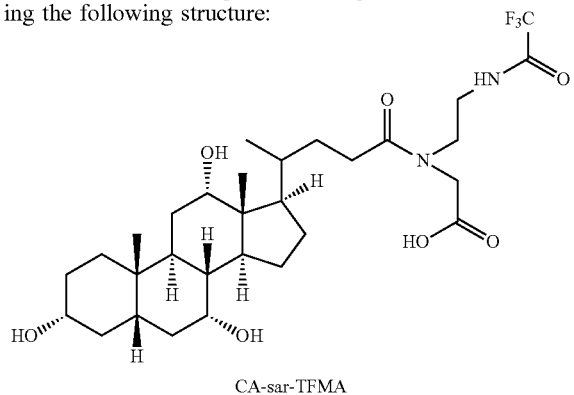

CA-sar-TFMA wherein CA-sar-TFMA is a $^{19}$F magnetic resonance imaging agent. The trifluorinated bile acid analogue may be formulated in conventional pharmaceutical administration forms, such as tablets, capsules, powders, solutions, suspensions, dispersions, and syrups in physiologically acceptable carrier media.

In another aspect the present invention provides for a method to diagnose impaired intestinal bile acid uptake, the method comprising:
a. administering a CA-sar-TFMA compound having the following structure

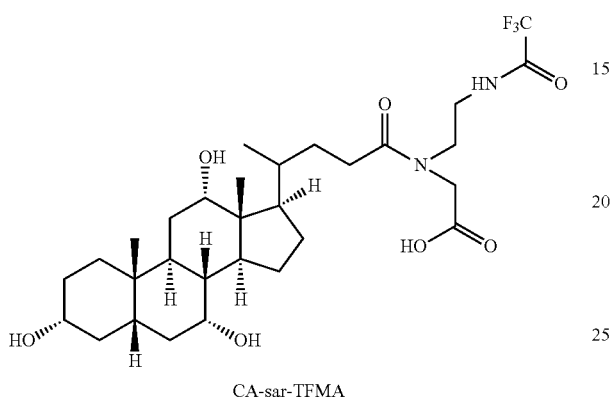

CA-sar-TFMA to a patient and then subjecting the patient to MRI to provide magnetic resonance images. The magnetic resonance images are then interpreted in comparison to baseline MRI studies to determine the mechanisms underlying BAM. Also, the method can be used to monitor the progression of the disease state in a patient and continuing pharmacological activity of anti-BAM agents over the course of time.

In a further aspect, the present invention provides for a method for treating an abnormality of a hepaticobiliary system, comprising: positioning a MRI probe having the following structure:

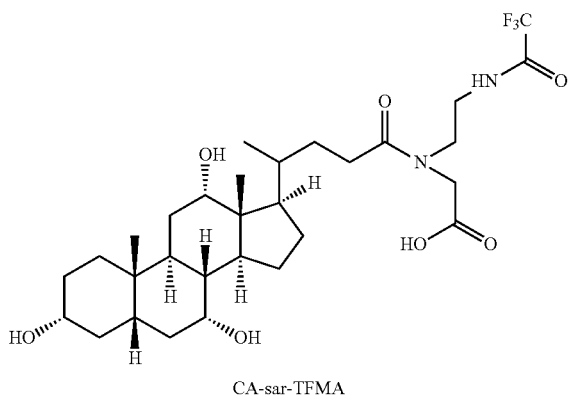

CA-sar-TFMA within the hepaticobiliary system; generating MRI probe signals that produce an image of the abnormality; and directing a therapeutic intervention towards the abnormality guided by the image of the abnormality produced from the MRI signals.

In a still further aspect the present invention provides for a method for diagnosis of bile acid diarrhea caused by at least the failure of enterohepatic recycling of the bile acids and excess amounts entering the colon of a subject, the method comprising:

administering a CA-sar-TFMA compound, having the following structure

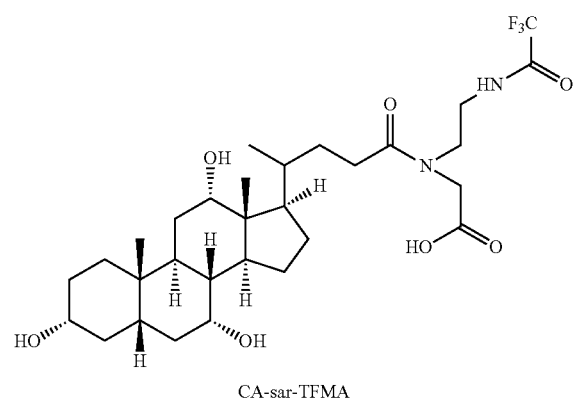

CA-sar-TFMA to a patient and then subjecting the patient to MRI to provide magnetic resonance images. The magnetic resonance images are then interpreted in comparison to base line MRI studies to monitor the progression of the disease state in a patient and evaluating reabsorption of bile acids into enterohepatic system.

In yet another aspect, the present invention provides for evaluating the function of an anti-BAM drug, such as a sequestrant, in a patient comprising:
a) administering CA-sar-TFMA to a patient, wherein CA-sar-TFMA has the following structure

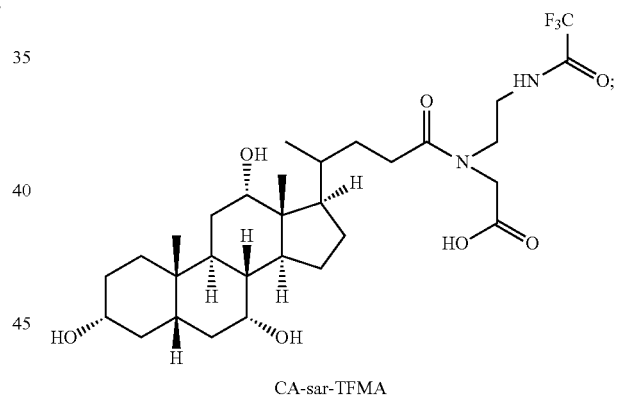

CA-sar-TFMA b) subjecting the patient to an MRI procedure; and
c) evaluating the function of the anti-BAM drug by comparing the MRI results with prior results from the patient or to a baseline MRI.

The results can also be used to determine the mechanisms underlying the BAM disease process and/or the functionality of anti-BAM agents. The processes can conveniently be used to monitor the progression of the disease state in a patient and continuing pharmacological activity of anti-BAM agents over the course of time. Some available bile acid sequestrants include but are not limited to Cholestyamine, Colestipol and Colesevelam.

In another aspect, the present invention provides for a method of improving the effectiveness of magnetic resonance imaging (MRI) of a patient's gallbladder which comprises:
a) administering an effective amount of CA-sar-TFMA to the patient, wherein CA-sar-TFMA has the following structure:

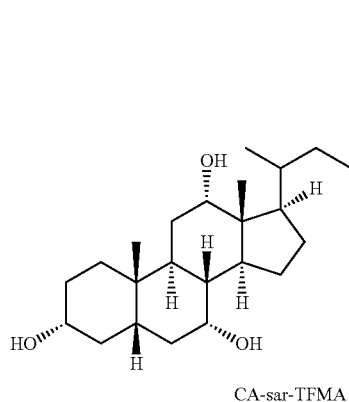

CA-sar-TFMA b) subjecting the gallbladder of the patient to an MRI where the administered CA-sar-TFMA is expected to accumulate; and c) evaluating the gallbladder from the magnetic resonance images obtained.

In a further aspect, the present invention provides a method to determine if the cause of chronic diarrhea is due to bile acid malabsorption, the method comprising:

administering CA-sar-TFMA having the following structure

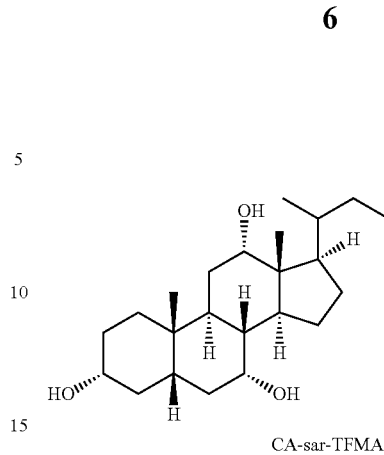

CA-sar-TFMA to a patient and then subjecting the patient to MRI, wherein the MRI results are interpreted in comparison to baseline MRI studies to evaluate the reabsorption of bile acids into enterohepatic system and/or concentration amount in the colon.

In the above methods, the baseline MRI studies can be, for example, from a normal subject not suffering from BAM, from a different subject who has BAM, or from a different subject whose BAM is being treated with an anti-BAM drug (e.g., a patient for whom the BAM is ameliorated by the anti-BAM drug). The baseline can also be the patient's own prior results (e.g., prior to treatment with an anti-BAM drug).

In a still further aspect, the present invention provides for a kit comprising an effective amount of CA-sar-TFMA for administration into different body tissues, ducts or cavities of a subject to monitor movement of bile acids, wherein CA-sar-TFMA has the following structure:

Other aspects, features and embodiments of the invention will be more fully apparent from the ensuing disclosure and appended claims.

DETAILED DESCRIPTION OF THE INVENTION

Figure 1:
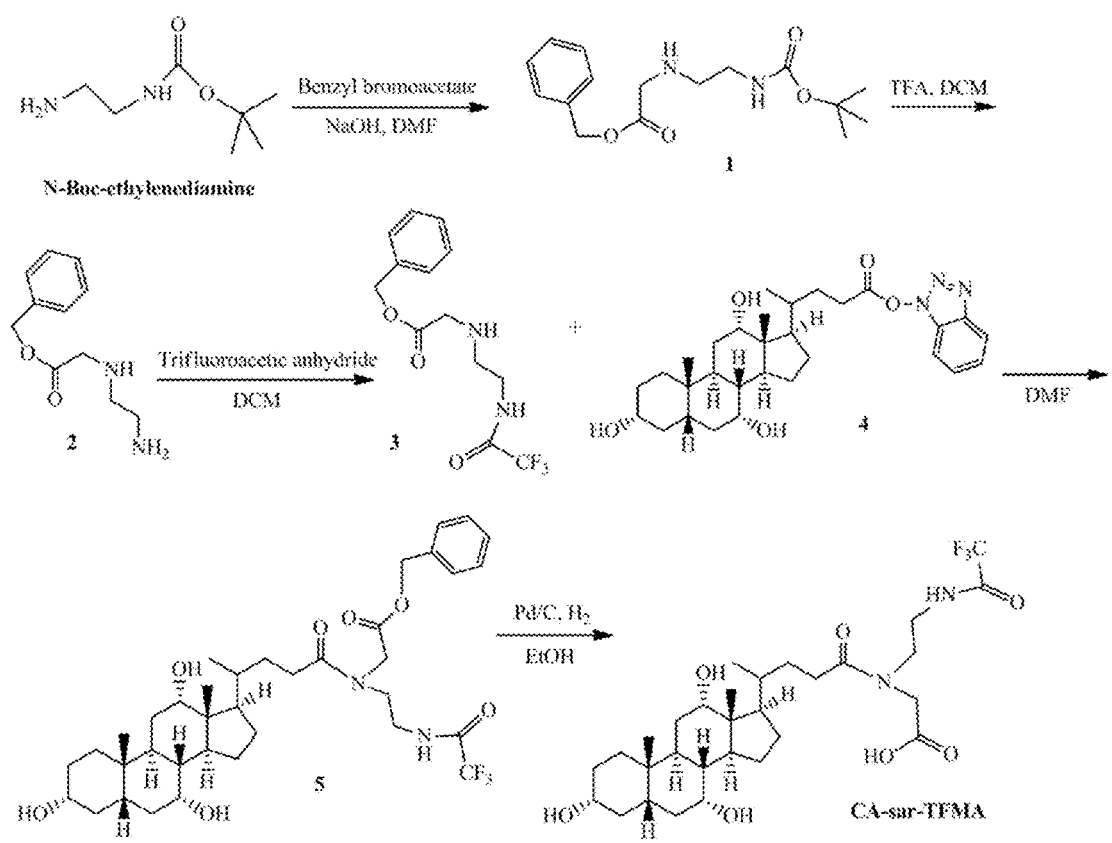
FIG. 1 shows the synthesis of CA-sar-TFMA (Cholic acid-sarcosine-trifluoro-N-methyl-acetamide). N-Boc-ethylenediamine was first reacted with benzyl bromoacetate, then the N-Boc group was removed with TFA. The free amine was trifluoroacetylated, and the resulting product was conjugated to an activated OBt ester form of cholic acid. To form the final product, the benzyl group in compound 5 was removed by catalytic hydrogenation.

The present invention provides for a trifluorinated bile acid analogue used as an imaging probe that is resistant to bacterial deconjugation. This resistance to bacterial deconjugation will diminish the potential for intestinal microbiota to alter probe concentrations in the enterohepatic circulation and also increase the half-life of the fluorinated bile acid analogue probe. The trifluorinated bile acid analogue CA-sar-TFMA exhibits in vitro stability and affinity for both ASBT and NTCP. A pilot in vivo disposition study in mice confirmed that CA-sar-TFMA can be imaged in the gallbladder using $^{19}$F MRI. Additionally, using Asbt-deficient mice as a test model, it is shown herein that oral administration of CA-sar-TFMA can provide a novel method to diagnose impaired intestinal bile acid uptake. Thus, collectively, the results shown herein support the suitability of CA-sar-TFMA as a $^{19}$F MRI tracer to diagnose BAM.

Notably, $^{19}$F MRI was chosen because it is non-invasive and involves no ionizing radiation. Thus, $^{19}$F MR images arise only from exogenously administered imaging probes, which offers a clear advantage over $^1$H-MRI techniques, since the $^1$H background signal (e.g., from water and lipids) is high in biological tissue. Unlike $^1$H MRI, with $^{19}$F MRI there is no endogenous background signal[16], thereby providing the potential for improved signal-to-noise-ratio. Furthermore, since the observed signal intensity directly correlates with $^{19}$F spin densities, $^{19}$F MRI permits quantitation of the administered $^{19}$F probe. Of particular interest is fluorine's diagnostic value in non-invasive imaging applications. $^{19}$F MRI signal intensity increases proportionally to fluorine concentration, so tracer amounts can be compared and quantified.[17]

Importantly, the fluorinated bile acid analogue imaging agent of the present invention combines the following features: non-toxic, biocompatible, chemically pure, and stable and high fluorine content. Additionally, the imaging agent meets an important $^{19}$F-MRI criterion, that being, a maximum number of chemically equivalent fluorines resonating at one or only few frequencies.

In one embodiment the trifluorinated bile acid analogue may be provided with a coating or matrix, such as a starch, polysaccharide material or a biotolerable polymer. Biodegradable coating or matrix materials are particularly preferred for particles which are to be administered parenterally while the polymer matrices and coating materials are particularly preferred for oral administration.

The CA-sar-TFMA imaging probe of the present invention may be administered by any route, such as, by oral or parenteral routes, although oral delivery is preferred. Where the CA-sar-TFMA imaging probe is to be provided parenterally, such as by intravenous, subcutaneous, intramuscular, intraventricular, intranasal or by aerosol administration, the CA-sar-TFMA imaging probe preferably is provided in an aqueous solution. The solution is physiologically acceptable so that in addition to delivery of the CA-sar-TFMA imaging probe to the patient, the solution does not otherwise adversely affect the patient's electrolyte and/or volume balance.

Useful solutions for parenteral administration may be prepared by any of the methods well known in the pharmaceutical art, described, for example, in Remington's Pharmaceutical Sciences (Gennaro, A., ed.), Mack Pub., 1990. Formulations of the CA-sar-TFMA imaging probe may include any compound or excipient that does not interfere with the MR imaging of the CA-sar-TFMA imaging probe, for example, polyalkylene glycols such as polyethylene glycol, oils of vegetable origin, alcohols and the like. An aqueous medium may comprise normal physiologic saline and preferably formulated as sterile aqueous solutions or suspensions having a pH from about 6.0 to 8.5. Such an aqueous solution containing the CA-sar-TFMA imaging probe can be made, for example, by dissolving CA-sar-TFMA in 50% ethanol or equivalent aqueous type solvents.

In contrast to other MRI enhancing agents known in the art which have required intravenous administration, a key feature of the present invention is that the CA-sar-TFMA imaging probe may be administered enterally with retention of image enhancement properties. As used herein, the term enteral administration implies administration of the CA-sar-TFMA imaging probe in active and bioavailable form to the gastrointestinal tract of a subject to be imaged. Thus, the CA-sar-TFMA imaging probe may be enterally administered orally, by gastric lavage or by other methods providing delivery of the CA-sar-TFMA imaging probe to the hepatobiliary and/or gastrointestinal region of the subject.

For the oral administration, the CA-sar-TFMA imaging probe can be formulated according to preparation methods conventionally used in pharmaceutical technique, possibly also as coated formulations to obtain an additional protection against the stomach acidic pH. Other excipients, such as viscosity modifiers, flavourings, pH adjusting agents, osmolality regulators, stabilizers, antioxidants, buffers and emulsifying or dispersing agents as well as other conventional pharmaceutical or veterinary formulation aids.

The formulated compositions contain an effective amount of the CA-sar-TFMA imaging probe of the present invention. That is, they contain amounts that provide appropriate concentrations of the CA-sar-TFMA imaging probe to provide sufficient time to image the positioning and/or movement of the CA-sar-TFMA imaging probe within the gastrointestinal tract and/or hepatobiliary system. Further, the concentration will vary depending upon a number of factors, including the formulation of the excipients, the administration route, including whether the CA-sar-TFMA imaging probe will be administered orally or systemically.

As a general matter, the preferred dosages of the CA-sar-TFMA imaging probe used according to the present invention will vary over a wide range and the chosen dosage will depend upon such factors as the administration route, the nature of the subject, the biodistribution, pharmacokinetics and the magnetic field strength and pulse sequence used in the imaging routine. For most conditions, dosage levels of the contrast enhancing agents will range from about 1 to about 250 mg per kg of body weight of the subject to be treated, more preferably from about 5 to about 200 mg per kg of body weight, and most preferably from about 10 to about 150 mg per kg of body weight.

The CA-sar-TFMA imaging probe of the present invention may be formulated in conventional pharmaceutical administration forms, such as tablets, capsules, powders, solutions, suspensions, dispersions, syrups, etc.; however, if solutions, suspensions and dispersions are used they may be combined with physiologically acceptable carrier media, for example water or physiological saline.

Solid dosage forms for oral administration may include enterally coated capsules, tablets, pills, powders and granules. In such solid dosage forms, the CA-sar-TFMA imaging probe may be admixed with at least one inert diluent such as sucrose, lactose or starch. Such dosage forms can also comprise, as in normal practice may also comprise buffering agents.

Liquid dosage forms for oral administration include pharmaceutically acceptable emulsions, solutions, suspensions, syrups and elixirs containing inert diluents commonly used in the art, such as water, in which the CA-sar-TFMA imaging probe of the present invention has been protected from deactivation in the stomach. Most commonly, the CA-sar-TFMA imaging probe will be protected from the stomach environment by a liquid form multiphase system, such a pharmaceutically acceptable micelle or liposome system. Beside the CA-sar-TFMA imaging probe and inert diluents, liquid based compositions may also include adjuvants, such as wetting agents, emulsifying and suspending agents, and sweetening, flavoring and perfuming agents, and other components known in the art.

After administration of the CA-sar-TFMA imaging probe of the present invention, magnetic resonance imaging is carried out in a conventional manner. The choice of pulse sequence (inversion recovery, IR; and spin echo, SE) and the values of the imaging parameters (echo time, TE; inversion time, TI; and repetition time, TR) will be determined by the nature and environment of the tissue to be imaged and the diagnostic information sought, as is known in the art.

The compounds used in the method of the invention can be prepared readily according in the following detailed examples using readily available starting materials, reagents and conventional synthetic procedures. The following examples illustrate the practice of the present invention but should not be construed as limiting its scope.

EXAMPLES

Materials

Taurocholate, cholic acid, trifluoroacetic anhydride, rat liver S9 fraction, trifluoroacetic acid, rat plasma, and choloylglycine hydrolase from *Clostridium perfringens* were obtained from Sigma Aldrich (St. Louis, Mo.). N-boc-ethylene diamine was purchased from Oakwood Chemical (West Columbia, S.C.). [$^3$H]-taurocholate (10 µCi/mM) was purchased from American Radiolabeled Chemicals, Inc. (St. Louis, Mo.). Trypsin, geneticin, fetal bovine serum (FBS) and Dulbecco's modified Eagle medium (DMEM) were purchased from Invitrogen (Rockville, Md.). All other reagents and chemicals were of the highest purity available commercially.

Methods

Synthesis of CA-sar-TFMA

CA-sar-TFMA was synthesized as in FIG. 1. 2 mL (12.6 mmol) N-boc-ethylene diamine was stirred for 15 min with 2 eq. (25.2 mmol) sodium hydroxide (NaOH) in dimethyl formamide (DMF). To this mixture, 0.6 eq. (7.6 mmol) benzyl bromoacetate was added and stirred overnight at room temperature. DMF was diluted with ethyl acetate and washed three times with 30 mL water. The product was dried with sodium sulfate and ethyl acetate was removed by vacuum. The resulting clear oil was separated by silica gel column chromatography, using an eluent of 1:1 ethyl acetate:hexane. The resulting product (FIG. 1, compound 1) showed an appropriate mass spectrometry (MS) peak of [M+1] 309.1.

Compound 1 was stirred with 1:1 dichloromethane (DCM):trifluoroacetic acid (TFA) for 15 min to remove the N-boc protecting group. Excess solvent was evaporated, yielding compound 2. Next, the compound was stirred in DCM at 0° C. and 0.6 eq. (3.5 mmol) trifluoroacetic anhydride was added. The mixture was allowed to return to room temperature and was stirred overnight. Dichloromethane (DCM) was then evaporated under vacuum and the product was dissolved in ethyl acetate and washed with saturated sodium bicarbonate. The organic layer was dried with sodium sulfate and ethyl acetate was evaporated under vacuum. The resulting product was purified using flash column chromatography with a solvent of 30% hexane in ethyl acetate. MS showed [M+1] of 305.1 (FIG. 1, compound 3) and thin layer chromatography (TLC) showed a single spot when stained with 10% w/v phosphomolybdic acid in ethanol (Rf=0.48; ethyl acetate).

Two g (4.9 mmol) cholic acid was stirred at room temperature for 15 min in dimethyl formamide (DMF) with 1 eq. (4.9 mmol) triethylamine (TEA) and 1 eq. (4.9 mmol) 0-benztriazol-1-yloxytris-1,1,3,3 tetra methyl uranium hexafluorophosphate (HBTU). 1 eq. (4.9 mmol) of hydroxybenzotriazole (HOBt) was added, and the mixture was stirred for 4 h, then the reaction was quenched with water and extracted with ethyl acetate. The organic layer was washed three times with water, dried with sodium sulfate, and solvent was evaporated under reduced pressure. Mass spectrometry (MS) of this resulting activated cholic acid OBt ester (FIG. 1, compound 4) showed a peak of [M+1] 526.4.

The activated OBt ester (3.4 mmol) was allowed to react with 1 eq. compound 3 (3.4 mmol) in DMF overnight at room temperature. The resulting product was extracted with ethyl acetate, washed three times with water, dried with sodium sulfate, and the ethyl acetate was evaporated under vacuum. Compound 5 was purified on a silica gel column using an eluent of 7% methanol in DCM, resulting in a fluffy white solid (MS showed [M+23] 717.3 and [M−1] 693.4). TLC confirmed purity, as a single spot was seen when stained with 10% w/v phosphomolybdic acid in ethanol (Rf=0.38; 10% methanol in DCM).

The final product, CA-sar-TFMA, was obtained by hydrogenating compound 5 in the presence of 10 weight percent palladium/carbon catalyst in ethanol (EtOH) for 4 h to remove the benzyl protecting group. Purity was confirmed by TLC, MS, high performance liquid chromatography (HPLC) and $^{13}$C nuclear magnetic resonance (NMR). Structural properties were confirmed with two-dimensional heteronuclear multiple-bond correlation spectroscopy (HMBC) and heteronuclear single quantum coherence (HSQC). NMR was performed on a Varian VNMRS 400 MHz machine (Agilent Technologies, Santa Clara, Calif.) in deuterated dimethyl sulfoxide (DMSO) at 25° C. HPLC was performed on a Waters HPLC system comprised of a 1525 binary HPLC pump, a 717 plus autosampler, and a 486 tunable absorbance detector (Waters Corporation, Milford, Mass.)

with a Restek column (ultra phenyl, 5 μm, 250×4.6 mm, Restek Corporation, Bellefonte, Pa.). Flow rate was 1.0 mL/min and absorbance wavelength was 218 nm. Two isocratic methods were used. The first method utilized 30% acetonitrile (ACN) and 70% water with 0.1% formic acid. The second method employed a 67:33 v/v mixture of methanol and [20 mM ammonium formate, 0.5% formic acid, 0.2% TEA (pH 3)]20. Both methods were linear from 25 to 200 μM (method one R2=0.998, method two R2=0.999).

Cell Culture

Stably transfected human apical sodium dependent bile acid transporter (hASBT)-Madin-Darby canine kidney (MDCK) cells were cultured at 37° C., 90% humidity, and 5% $CO_2$, as previously described.[21] Cells were fed every two days with Dulbecco's modified eagle medium (DMEM) fortified with 10% fetal bovine serum (FBS), 50 units/mL penicillin and 50 μg/mL streptomycin. Geneticin (1 mg/ml) was added to maintain selection pressure. Cells were passaged after reaching 90% confluency (approximately every 4 days). Stably transfected human Na+/taurocholate cotransporting polypeptide (hNTCP)-human embryonic kidney (HEK) cells were cultured in a similar manner, with the addition of 1% nonessential amino acids to the DMEM.[22] When 90% confluent, cells were seeded at a density of 0.6 million cells/well in 12-well plates (ASBT-MDCK cells) or at a density of 0.3 million cells/well in 24-well plates (NTCP-HEK). One day after seeding and 15 h prior to uptake studies, ASBT-MDCK cells were induced with 10 mM sodium butyrate. For both inhibition and uptake studies, three replicates were used for each donor concentration.

Inhibition of ASBT and NTCP

Both ASBT-MDCK and NTCP-HEK cells were exposed to donor solution 2 days after seeding Inhibition donor solutions consisted of Hank's balanced salt solution (HBSS) in the presence of 2.5 μM native bile acid taurocholate. Inhibition donor solutions were spiked with 0.5 μCi/mL [$^3$H] taurocholate.

Cells were washed three times with Hank's balanced salt solution (HBSS) and exposed to donor solution. After incubation at 37° C. (10 min for hASBT-MDCK cells and 5 min for hNTCP-HEK cells, periods of linear uptake for these transfected cell lines), wells were rinsed three times with cold sodium-free buffer (SFB). In SFB, sodium chloride was replaced with 137 mM tetraethylammonium chloride. Cells were lysed using ACN (300 μL for MDCK cells and 150 μL for HEK cells) and were left to evaporate at room temperature for 3 h. Wells were extracted with 1:1 ACN:water and counted for radioactivity using a LS6500 liquid scintillation counter (Beckmann Instruments, Inc., Fullerton, Calif.).

Resulting data were fitted to a modified Michaelis-Menten competitive inhibition equation to regress for compound Ki. No weighting was used, and regression was performed using Phoenix WinNonlin (Pharsight, St. Louis, Mo.). This modified equation (eqn. 1) accounts for aqueous boundary layer permeability, as previously described.[23]

$$V = \frac{P_{ABL} \cdot \left(\frac{V_{max}}{K_m(1+I/K_i)+S} + P_p\right)}{P_{ABL} + \frac{V_{max}}{K_m(1+I/K_i)+S} + P_p} \cdot S \quad \text{(eqn. 1)}$$

where V is taurocholate flux, $P_{ABL}$ is aqueous boundary layer permeability (measured previously as 1.5×10$^{-4}$ cm/s)[24], (not sure this is correct) S is taurocholate concentration (i.e. 2.5 μM), and $P_p$ is passive taurocholate permeability. $K_m$ was set as 5.03 μM for ASBT inhibition and 5.31 μM for NTCP inhibition, determined from historic data.[25,26] Pp was determined by taurocholate uptake in SFB on the same occasion, measured using a saturating concentration of 200 μM.

Uptake of CA-sar-TFMA by ASBT and NTCP

Uptake studies were similar to inhibition studies, except that donor solutions consisted of 0-200 uM CA-sar-TFMA in either HBSS or sodium free buffer (SFB) without taurocholate. Compound uptake in SFB was used to determine sodium-independent passive permeability, since both ASBT and NTCP are sodium-dependent uptake transporters. Cells were initially washed three times with either HBSS or SFB (consistent with donor), then exposed to donor solution and rinsed as described above. Extracts after cell lysing were stored at −80° C. in silanized centrifuge tubes until analysis by liquid chromatography/tandem-mass spectrometry (LC/MS/MS). Taurocholate Vmax was estimated using a saturating concentration of 200 μM on each study occasion. Taurocholate donor solutions were spiked with 0.5 μCi/mL [$^3$H] taurocholate.

Resulting uptake data were fitted to a modified Michaelis-Menten equation and regressed for $V_{max}$ and $K_m$ (eqn. 2).

$$V = \frac{P_{ABL} \cdot \left(\frac{V_{max}}{K_m+S} + P_p\right)}{P_{ABL} + \frac{V_{max}}{K_m+S} + P_p} \cdot S \quad \text{(eqn. 2)}$$

$$V = \frac{P_{ABL} P_p}{P_{ABL} + P_p} S \quad \text{(eqn. 3)}$$

HBSS uptake data (i.e. total uptake) were fitted using eqn. 2. V is substrate flux, $P_{ABL}$ is 1.5×10$^4$ cm/s, as defined above, and Pp is passive permeability. Pp was estimated using eqn. 3 and SFB uptake data (i.e. sodium-independent uptake). After regression, Vmax was normalized against the Vmax of taurocholate on the same occasion, to account for variability in transporter expression. The resulting Vmax is expressed as norm Vmax.

Stability of CA-sar-TFMA

5 μM of CA-sar-TFMA was incubated in 1 mL simulated intestinal fluid (SIF) with pancreatic enzymes, rat plasma, rat liver s9 fraction (1 mg/mL) with 1 mM nicotinamide adenine dinucleotide phosphate (NADPH) in Dulbecco's phosphate buffered saline (DPBS), and 0.1 M HCl to simulate stomach conditions (n=3 for each). SIF, prepared according to the previously modified USP28 method', consisted of 0.2 M NaOH, 6.8 g/L monobasic potassium phosphate, and 10 g/L pancreatin, adjusted to pH 7.5. In each of these studies, 1 mL solutions were incubated at 37° C. before adding CA-sar-TFMA to start the experiment, yielding 5 μM CA-sar-TFMA. At time t=0 h and t=4 h, 100 μL of CA-sar-TFMA in stability media was removed and added to 400 μL of cold acetonitrile. Samples were centrifuged at 12,000 g for 5 min, stored at −80° C., and then analyzed by LC/MS/MS.

CGH, a bacterial bile-acid deconjugating enzyme, was used to simulate conditions in the colon. CGH is found in small amounts in the terminal ileum and more abundantly in the colon. Stability of CA-sar-TFMA was evaluated in CGH from *Clostridium perfringens*. Previously, CA-lys-TFA was shown to be susceptible to deconjugation by CGH.[15] Ten mM mercaptoethanol, 1 mM ethylenediaminetetraacetic acid (EDTA), and CA-sar-TFMA were added to 5 mM sodium acetate buffer at pH 5.6 (n=3), yielding 2 mM CA-sar-TFMA.[28] After incubation at 37° C., the study was started by adding 15 U CGH. The stability of CA-lys-TFA was examined in parallel under the same conditions for comparison. 100 µL samples were removed at t=0, 15 min, 30 min, 1 h, 2 h, 3 h, and 4 h and diluted with 400 µL cold acetonitrile. Samples were centrifuged at 12,000 g for 5 min and analyzed by LC/MS/MS.

CA-sar-TFMA Solubility in Buffer

Five (5) mg of compound was added to silanized centrifuge tubes containing 100 µL phosphate buffer at pH 6.8 (n=3), shaken, and left overnight at room temperature. Subsequently, tubes were centrifuged at 12,000 g for 5 min. Supernatant was diluted 10,000-fold with 1:1 ACN:water and analyzed by LC/MS/MS.

In Vitro $^{19}$F MR Phantom Imaging

To evaluate the $^{19}$F imaging signal intensity of CA-sar-TFMA, 30 mM of CA-sar-TFMA and 30 mM of CA-lys-TFA dissolved in methanol were imaged adjacent to one another on the same occasion in 2-mL glass vials (12-mm diameter, National Scientific, Rockwood, Tenn.).

Oral Disposition Characterization of CA-sar-TFMA: Pilot Study

All animal studies were approved by the Institution Animal Care and Use Committee of both the University of Maryland School of Medicine and the Research and Development Committee at the VA Maryland Health Care System, in accordance with the Guide for the Care and Use of Laboratory Animals prepared by the U.S. National Academy of Sciences.[29] Six male C57BL/6 mice (average age 20.6 weeks, average weight 26.8 g) were purchased from Jackson Laboratories (Bar Harbor, Me.). Mice were housed with free access to water and standard mouse chow in a pathogen-free environment with a 12:12-hour light/dark cycle for one week prior to experiments.

After an overnight fast, mice were gavaged with 150 mg/kg CA-sar-TFMA in vehicle [60% polyethylene glycol (PEG)400 and 40% DPBS, 8.33 µL per g mouse body weight]. Mice 1-5 were maintained in the fasted state, and anaesthetized at 7 h after dosing with ketamine/xylazine and exsanguinated by intracardiac puncture. Blood was collected into heparinized tubes and centrifuged at 12,000 g for 10 min. Supernatants were analyzed by LC/MS/MS. Additionally, liver and gallbladder were removed and homogenized on ice with a glass tissue homogenizer (Duall size-21, Kimble Chase Life Science, Vineland, N.J.). Imaging agent was extracted with 75% ACN in water (800 µL for liver and 300 µL for gallbladder). Extracts were centrifuged at 12,000 g for 10 min and analyzed by LC/MS/MS.

Murine Gallbladder Imaging

After fasting and gavage as described above, mouse 6 was anaesthetized with ketamine/xylazine by intraperitoneal (IP) catheter injection and subjected to $^1$H MRI at 6.2 h after dosing. $^{19}$F MRI was performed 6.7 h after dosing (1.5 h total $^{19}$F acquisition time). Approximately every 30 min throughout imaging, maintenance doses of ketamine/xylazine were infused through the IP catheter. The mouse remained in the MRI machine for 2 h, including coil tuning time and $^1$H and $^{19}$F signal acquisition time. A 30 mM phantom of CA-sar-TFMA dissolved in methanol in a short glass NMR tube (5-mm diameter) was imaged alongside the mouse on the same occasion. After imaging, mouse euthanasia and tissue harvesting proceeded as described above. Tissues were analyzed by LC/MS/MS.

Asbt Knockout Mice

Asbt-deficient (Slc10a2−/−) mice were obtained from a colony maintained at the Wake Forest School of Medicine. Four knockout mice (age 46.2±3.3 weeks, weight 27.0±1.4 g) and four wild-type (WT) littermates (age 43.8±2.3 weeks, weight 29.5±1.3 g) were fasted overnight and gavaged with 150 mg/kg CA-sar-TFMA in vehicle (3:2 PEG:DPBS). Gallbladder, liver, and plasma samples were collected at 7 h after dosing, and tissues were processed as described above and analyzed by LC/MS/MS.

MRI

All in vitro and in vivo MRI data were acquired using identical parameters, as described previously[18] (i.e. phantom and animal experiments used identical $^{19}$F and $^1$H parameters). Briefly, MRI experiments were performed on a Bruker BioSpec 70/30USR Avance III 7T horizontal bore MR scanner (Bruker Biospin MRI GmbH, Germany) with a BGA12S gradient system and used Bruker ParaVision 5.1 software for acquisition and processing. The coil was a Bruker 40-mm $^{19}$F/$^1$H dual-tuned linear volume coil that transmitted and received radiofrequency (RF) signals at 300.28 MHz for $^1$H and 282.55 MHz for $^{19}$F nuclei. Multi-slice $^1$H MR images used an acquisition time of 7 min and 15 s using a RARE (rapid acquisition with relaxation enhancement) sequence in the cross view of the phantom or animal body. $^1$H MRI employed repetition time 2200 ms, RARE factor 8, field of view 4×4 cm$^2$, echo time 8.9 ms, slice thickness 1.0 mm, matrix size 266×266, number of averages 6, and in-plane resolution 150×150 µm$^2$. $^{19}$F images were acquired with a FLASH (fast low angle shot) sequence in an identical region to $^1$H MRI. $^{19}$F acquisition time was 1 h and 30 min. Parameters were the same as $^1$H MRI, but with repetition time 220 ms, echo time 3.078 ms, in-plane resolution 1.25×1.25 mm$^2$, matrix size 32×32, slice thickness 4.0 mm, number of averages 768, and flip angle=30°. The flip angle was optimized using the T1 relaxation time of the phantom. For the in vivo mouse imaging experiment, the phantom was a 5-mm diameter shortened glass NMR tube containing 30 mM CA-sar-TFMA dissolved in methanol.

CA-sar-TFMA concentration in the gallbladder of mouse 6 was calculated by comparing the mean signal intensity in the region of interest (ROI) identified in the gallbladder to the mean signal intensity in the phantom ROI imaged next to the mouse body. In each case, the region of interest (ROI) was drawn to exclude the edges of phantom and gallbladder, so that signal intensity calculation did not suffer from a partial volume edge effect due to the image resolution. Mean signal intensity was calculated with Bruker ParaVision 5.1. The limit of quantification of $^{19}$F signal for this method was previously determined to be 6.82 mM[18], which corresponds to the noise magnitude of an ROI on the image periphery plus 2.5-times its standard deviation. Using this method, there is greater than 99% confidence that voxels with concentrations above this limit represent real $^{19}$F signal, and not noise.[30]

Medical Image Processing, Analysis and Visualization software (MIPAV v7.0.1, CIT, NIH, Bethesda, Md.) was used to generate a color $^{19}$F MR image of mouse 6 and adjacent phantom. The image threshold used was 0.7 on a scale where the strongest signal (in red) was 1.0.

LC/MS/MS Analysis

CA-sar-TFMA concentrations, as well as CA-lys-TFA and cholic acid from CGH stability testing, were quantified with LC/MS/MS using a Waters Acquity UPLC system with triple quadrupole detector (Waters Corporation, Milford, Mass.). The column used was a Waters Acquity UPLC Ethylene Bridged Hybrid C8 1.7 µm 2.1×50 mm column (0.4 mL/min flow rate, 10 µL injection volume). CA-sar-TFMA, CA-lys-TFA, and cholic acid were quantified with negative electrospray ionization, each employing a multiple reaction monitoring (MRM) method. For CA-sar-TFMA, the transition 603.53 Da to 213.12 Da was monitored (dwell time 0.1 s, cone voltage 65 V, collision energy 36 V). For CA-lys-TFA, the transition 631.31 Da to 241.07 Da was monitored (dwell time 0.1 s, cone voltage 70 V, collision energy 40 V). For cholic acid, the transition 407.09 Da to 343.24 Da was monitored (dwell time 0.1 s, cone voltage 70 V, collision energy 34 V). For each method, the eluent used was a combination of water with 0.1% formic acid (A) and ACN with 0.1% formic acid (B). The gradient expressed as % B was as follows: initially 50% until 0.5 min, then increased to 95% at 1.5 min, decreased to 50% at 1.7 min, and maintained at 50% until 2.0 min. The methods were linear between 10 and 2000 nM (CA-sar-TFMA, R2=0.9995; CA-lys-TFA, R2=0.9998; cholic acid, R2=0.9931).

Statistical Analysis

Error shown in the text and figures is standard error of the mean throughout. The Student's paired t-test was used to analyze data resulting from in vitro stability assays, while the Student's unpaired t-test was used to evaluate knockout versus wild type mouse data. A P-value of 0.05 or lower was considered significant.

Results

Synthesis of CA-sar-TFMA

CA-sar-TFMA was successfully synthesized. When stained with 10% w/v phosphomolybdic acid in ethanol, TLC showed a single spot that did not move using a solvent of 10% methanol in DCM. MS analysis showed appropriate peaks of [M+23] 627.3 and [M−1] 603.4, and confirmed that no cholic acid was present. The first HPLC method had RT=2.94 min, while the second showed RT=3.62 min (purity 99.0%).

Figure 9:
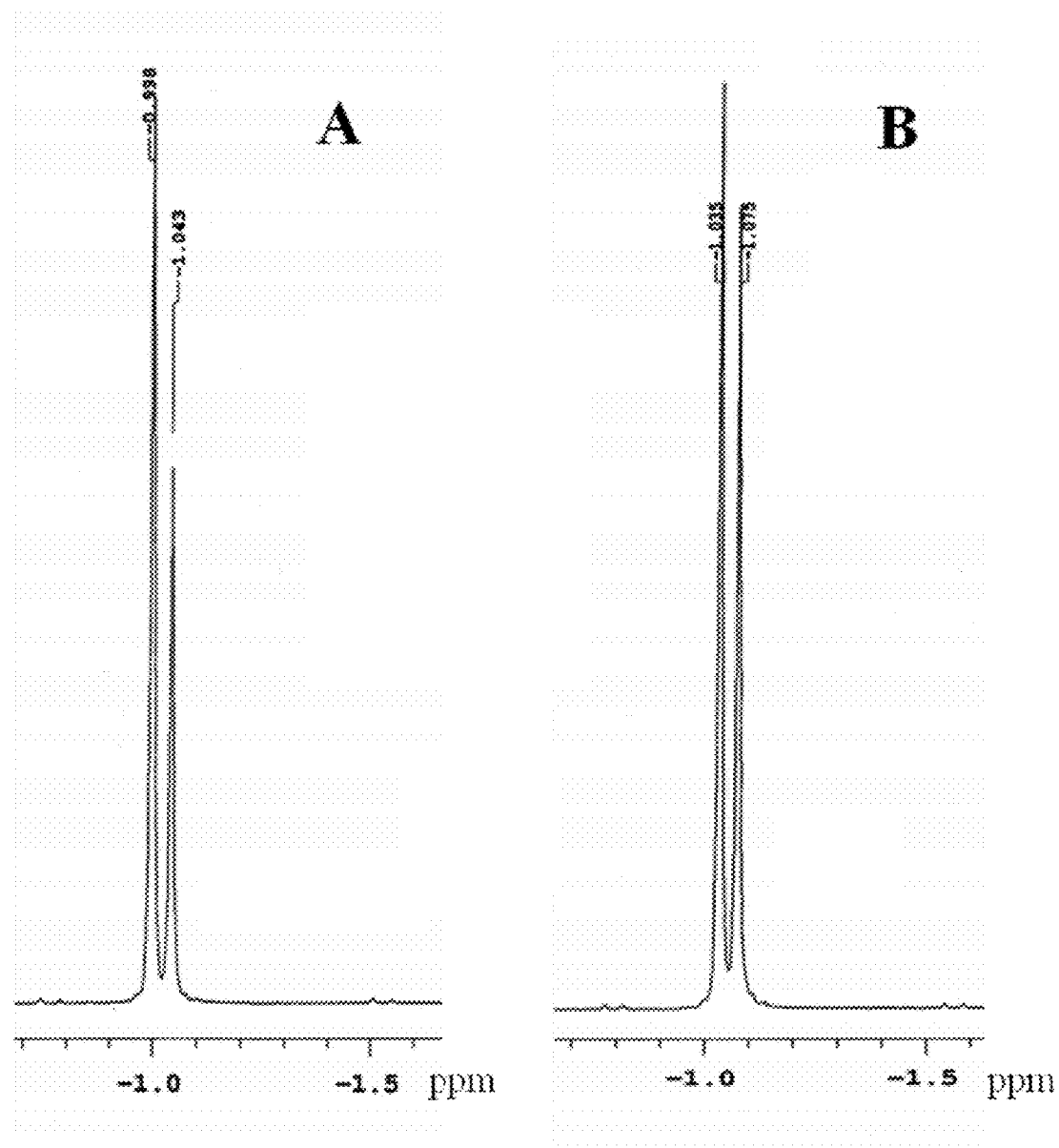
FIG. 9 shows $^{19}$F NMR spectra of compound 5 (spectrum A) and CA-sar-TFMA (spectrum B). The $^{19}$F NMR spectra suggest that the two compounds exist as two rotational isomers, but with a different isomer equilibrium for CA-sar-TFMA (spectrum B) carboxylic acid than for the protected benzyl ester (spectrum A).

$^{13}$C NMR and two-dimensional analysis showed two rotational isomers of CA-sar-TFMA. Thus, like other drugs, e.g. valsartan[31], CA-sar-TFMA appears to have two different rotational states around a tertiary amide bond that yields split peaks for carbon atoms. Tertiary amide bonds often give rise to rotamers because of the inherent flexibility of the bond, and the inability to form stabilizing hydrogen bonds. Rotamers were present in almost equal amounts, with rotamer A (designated below) slightly more abundant than rotamer B. $^{13}$C NMR in DMSO-$d_6$, rotamer A: δ 12.78, 17.54, 23.06, 23.27, 26.64, 27.73, 28.97, 29.60, 30.84, 31.50, 34.82, 35.31, 35.46, 35.76, 38.07, 39.93, 40.00, 41.80, 41.95, 46.58, 46.20, 46.91, 47.56, 66.67, 70.87, 71.46, 117.72, 156.74, 171.45, 173.33. $^{13}$C NMR in DMSO-$d_6$, rotamer B: δ 12.78, 17.54, 23.06, 23.27, 26.64, 27.64, 28.97, 29.60, 30.84, 31.27, 34.82, 35.31, 35.46, 35.76, 37.68, 39.93, 40.00, 41.80, 41.95, 45.64, 46.20, 46.91, 50.10, 66.67, 70.87, 71.46, 114.86, 156.94, 171.87, 174.10. Hence, carbon atoms affected by rotamer formation were carbons 16, 22, and 24 of the cholic acid scaffold, along with all of the carbon atoms on the conjugated side chain (i.e. carbons 25-30). $^{19}$F NMR spectra of compound 5 (FIG. 1) and CA-sar-TFMA confirm the presence of two isomers both CA-sar-TFMA and its synthetic precursor (FIG. 9).

Inhibition of ASBT and NTCP

Figure 2:
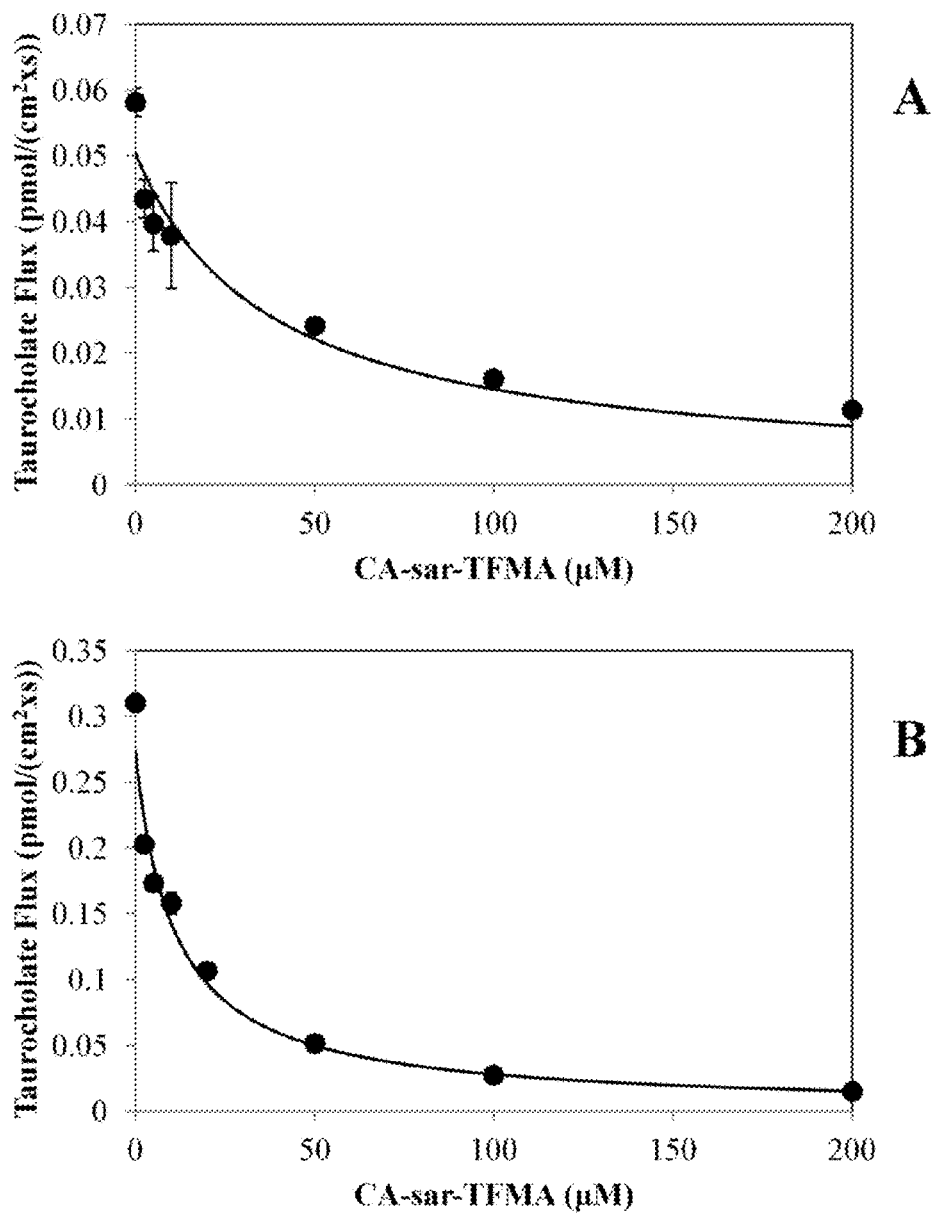
FIG. 2 shows the inhibition of taurocholate uptake by ASBT (panel A) and NTCP (panel B) by CA-sar-TFMA. Regression analysis showed ASBT Ki=21.5±4.0 µM and NTCP Ki=2.64±0.55 µM. Each point represents n=3 samples.

CA-sar-TFMA was a potent inhibitor of both ASBT and NTCP. FIG. 2 shows the results of the inhibition of taurocholate uptake by CA-sar-TFMA in stably transfected ASBT-MDCK cells (panel A) and stably transfected NTCP-HEK cells (panel B). Regression analysis showed ASBT Ki=21.5±4.0 μM and NTCP Ki=2.64±0.55 μM.

Uptake of CA-sar-TFMA by ASBT and NTCP

Figure 3:
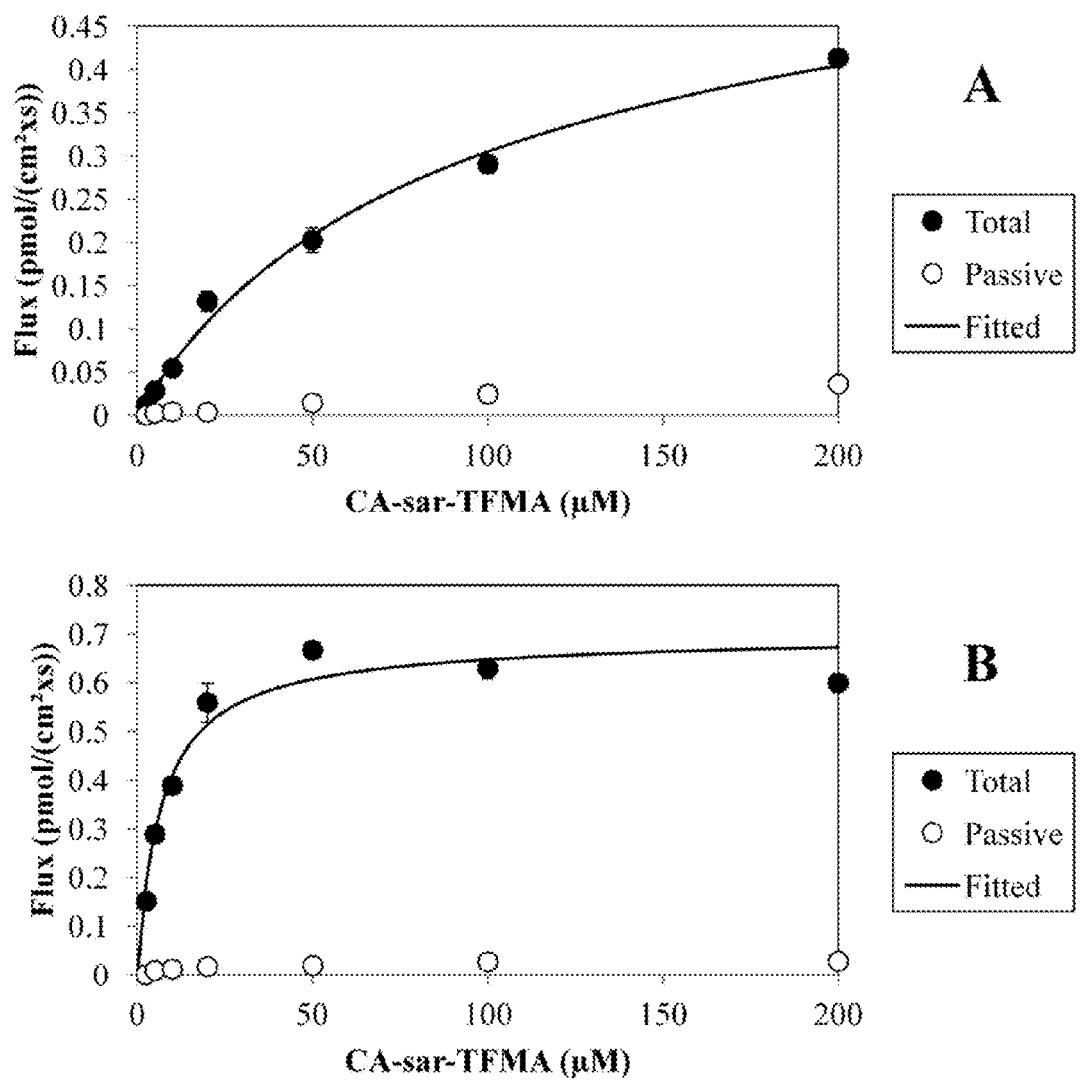
FIG. 3 shows the uptake of CA-sar-TFMA by ASBT (panel A) and NTCP (panel B). Regression analysis showed ASBT Km=73.2±7.0 µM and NTCP Km=2.19±0.63 µM. Each point represents n=3 samples.

FIG. 3 shows the results of uptake of CA-sar-TFMA by ASBT (panel A) and NTCP (panel B). Regression analysis showed ASBT Km=73.2±7.0 μM, passive permeability (Pp)= 2.10×10$^{-7}$ cm/s, and normVmax (normalized to taurocholate Vmax on the same occasion)=1.50. For NTCP uptake, Km=2.19±0.63 μM, Pp=0.43×10$^{-7}$ cm/s, and norm-Vmax=0.24. For comparison, in the same cell lines the native bile acid taurocholate has Km values of 5.03 μM[32] and 5.31 μM[33] for ASBT and NTCP, respectively.

Stability of CA-sar-TFMA

Figure 4:
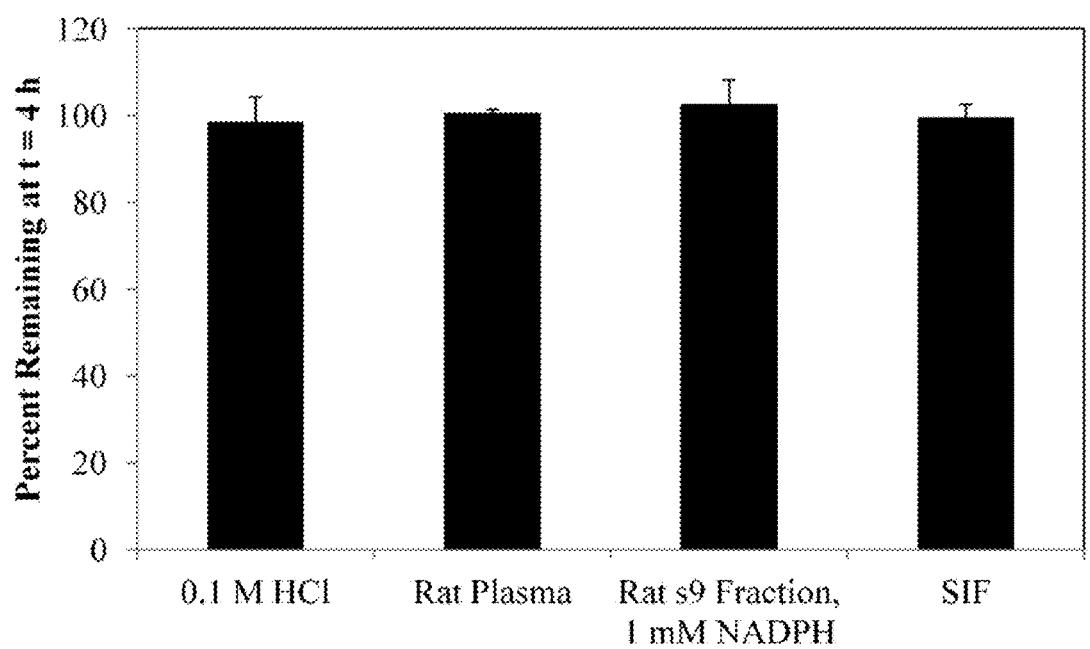
FIG. 4 shows the in vitro stability of CA-sar-TFMA. Concentration of CA-sar-TFMA at t=4 h was not different from initial concentration in 0.1 M HCl, rat plasma, rat s9 fraction with 1 mM NADPH, or simulated intestinal fluid with pancreatic enzymes (SIF) (P>0.3 for Student's paired t-test). Each point represents n=3 samples.

In FIG. 4, results are shown from stability analysis of CA-sar-TFMA in 0.1 M HCl, rat plasma, rat liver s9 fraction with 1 mM NADPH, and SIF. The novel bile acid analog showed favorable stability in each environment with no evidence of degradation. Using the Student's paired t-test, concentrations of CA-sar-TFMA at t=4 h were not significantly different from starting concentrations. The lowest one-tailed P-value observed was 0.30.

Figure 5:
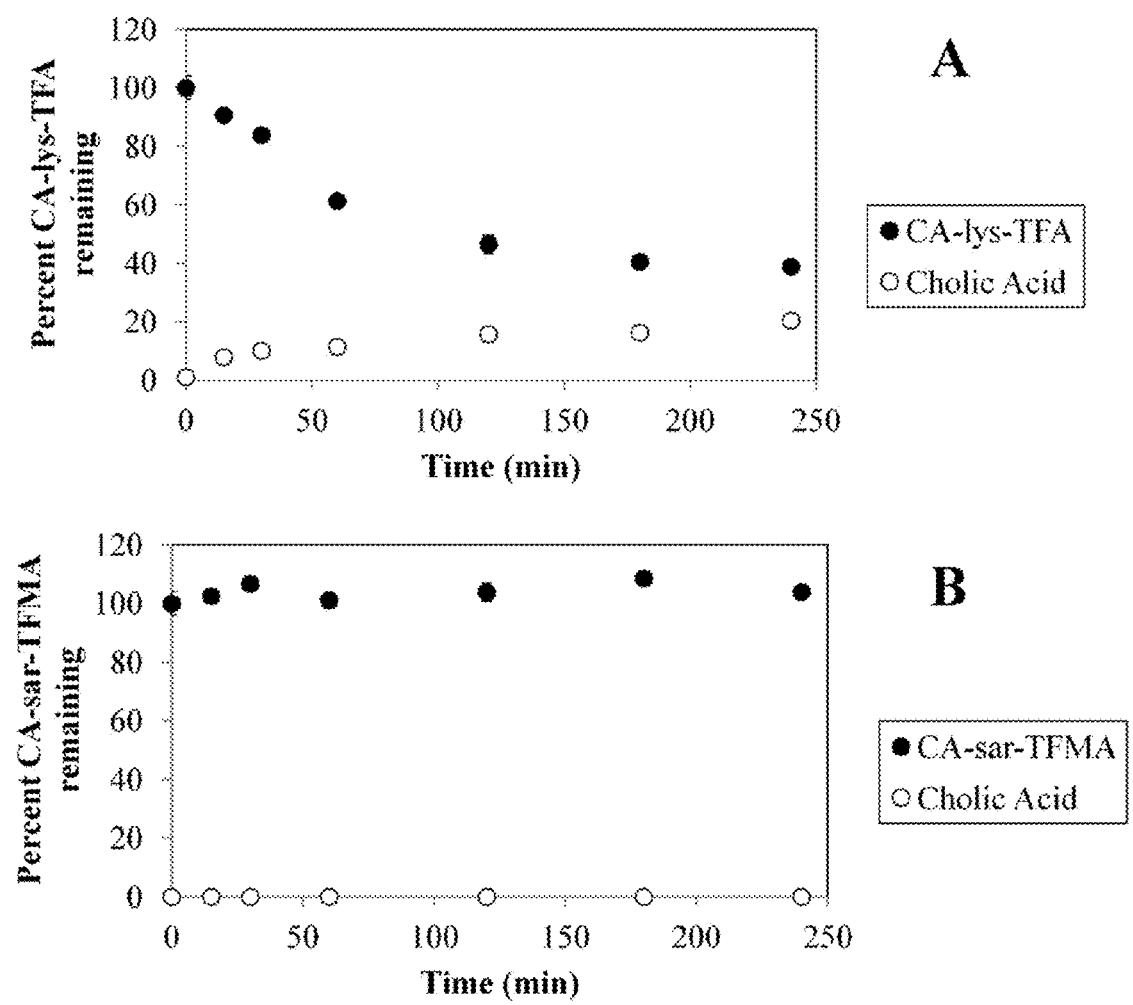
FIG. 5 shows the stability of CA-sar-TFMA (panel A) and CA-lys-TFA (panel B) in the presence of choloylglycine hydrolase. After 4 h, 103.9±2.9% of CA-sar-TFMA remained, with no detectable release of cholic acid. In contrast, 38.9±0.2% of CA-lys-TFA remained after 4 h, with 20.5±0.3% release of cholic acid. Each point represents n=3 samples.

In FIG. 5, results of CA-sar-TFMA stability against CGH are shown. After 4 h, 38.9±0.2% of CA-lys-TFA remained, with 20.5±0.3% release of cholic acid (shown in Panel A). In contrast, 103.9±2.9% of CA-sar-TFMA remained, with no release of cholic acid (shown in Panel B). Therefore, CA-sar-TFMA showed improved in vitro stability over CA-lys-TFA in response to bile acid deconjugation by CGH. It is theorized that the tertiary amide bond linkage to cholic acid in CA-sar-TFMA afforded this improved stability compared to CA-lys-TFA, which possesses a secondary amide bond linkage.

CA-sar-TFMA Solubility in Buffer

Solubility in phosphate buffer at pH 6.8 was measured to be 33.5±1.6 mM, above the $^{19}$F limit of quantification of approximately 5 mM trifluorinated compound (i.e. 15 mM fluorine atoms) determined previously with the same equipment and MRI parameters used here.[18]

In Vitro $^{19}$F MR Phantom Imaging

Figure 6:
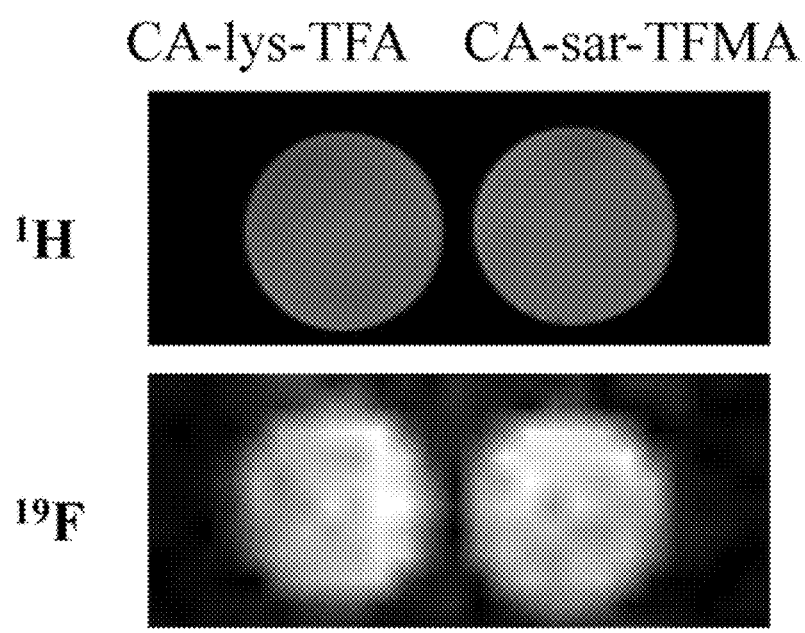
FIG. 6 shows $^1H$ and $^{19}F$ MRI of fluorinated bile acids. 2-mL glass vials of 30 mM CA-lys-TFA and 30 mM CA-sar-TFMA were imaged adjacent to one another on the same occasion. Analysis of $^{19}F$ MR images using Bruker ParaVision 5.1 showed that CA-lys-TFA and CA-sar-TFMA phantoms provided identical average signal intensities. This equivalence in intensities reflects that both compounds contain three equivalent fluorines (i.e. possess identical number of fluorine atoms).

An MR phantom image of 30 mM CA-sar-TFMA adjacent to 30 mM CA-lys-TFA is shown in FIG. 6. Each is dissolved in methanol in 2-mL glass vials. This figure demonstrates that, although the CA-sar-TFMA has a split fluorine peak, the total signal intensity is similar to that of CA-lys-TFA, which did not exhibit a split peak of its three equivalent fluorine atoms. CA-sar-TFMA peak splitting did not appear to affect MRI signal intensity, as anticipated since peak split only spanned 0.045 ppm or less. The $^{19}$F average ROI signal intensity of both CA-sar-TFMA and CA-lys-TFA were identical, at 2.66 each (arbitrary units).

Oral Disposition Characterization of CA-sar-TFMA: Pilot Study

CA-sar-TFMA showed high targeting to the mouse gallbladder at 7 h after oral dosing. Results are shown in Table 1 below which provides data for an in vivo pilot study 7 hours after oral administration of 150 mg/kg CA-sar-TFMA. CA-sar-TFMA showed high accumulation in the mouse gallbladder and was present in much lower amounts in liver and plasma.

| Mouse # | Gallbladder weight (mg) | Gallbladder Conc. (mM) | Liver Conc. (μM) | Plasma Conc. (μM) |
|---|---|---|---|---|
| 1 | 30 | 16.5 | 20.8 | 1.31 |
| 2 | 23 | 25.0 | 16.0 | 1.49 |
| 3 | 27 | 17.2 | 12.9 | 1.81 |

| Mouse # | Gallbladder weight (mg) | Gallbladder Conc. (mM) | Liver Conc. (µM) | Plasma Conc. (µM) |
|---|---|---|---|---|
| 4 | 36 | 16.9 | 9.5 | 0.94 |
| 5 | 30 | 16.5 | 13.5 | 1.47 |

Liver and gallbladder concentrations of CA-sar-TFMA were calculated by assuming an organ density of 1 g/mL. Average gallbladder concentration was 18.4±1.6 mM. In contrast, accumulation in the liver and plasma were on average at least 1,000-fold lower than in gallbladder. Average liver concentration was 14.5±0.6 µM, while average plasma concentration was 1.40±0.14 µM. Gallbladder concentrations were above the $^{19}$F MRI limit of detection for a trifluorinated compound, as previously defined[18], and liver and plasma concentrations were below the limit of detection.

Murine Gallbladder Imaging

Figure 7:
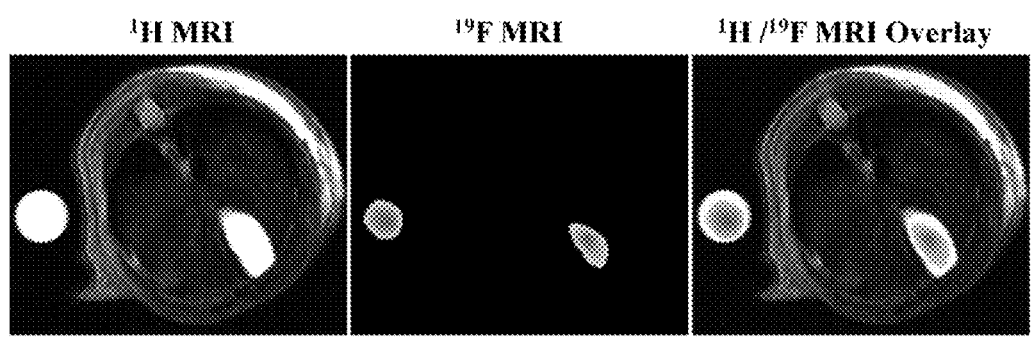
FIG. 7 shows CA-sar-TFMA in vivo MR images. The left-most panel shows a $^1H$ MR image of the cross section of a mouse's body, with a phantom of CA-sar-TFMA imaged adjacent to the body. The center panel shows the $^{19}F$ MR image of the same cross section. The right-most panel shows an overlay of the $^1$H and $^{19}$F images. CA-sar-TFMA signal intensity of the gallbladder region of interest (ROI) was normalized to the phantom ROI, and gallbladder concentration was calculated to be 34.2 mM.

Mouse 6 underwent MR imaging at 6.2-8.2 h after oral gavage of 150 mg/kg CA-sar-TFMA. In FIG. 7, a high concentration of CA-sar-TFMA was visualized in the gallbladder by $^{19}$F MRI (identified anatomically by its corresponding $^1$H image). Compound concentration was calculated by normalizing the average intensity of the gallbladder ROI to that within the phantom, and was determined to be 34.2 mM. After euthanasia, mouse gallbladder concentration was analyzed by LC/MS/MS to be 14.8 mM. This 2.3-fold lower concentration agrees with previous observations that LC/MS/MS-based gallbladder concentrations are typically 2.7(±0.8)-fold lower than those observed by MRI due to animal handling after imaging.[18] Since gallbladder emptying is a mechanical process, this previously-observed difference (on two independent occasions) in measured concentrations was attributed to partial emptying of the gallbladder as a consequence of animal handling (e.g., removal from the scanner, transport to a surgical facility, and the application of additional sedation before harvesting of tissue).[18] Corresponding liver and plasma CA-sar-TFMA concentrations for Mouse 6 were much lower than those in gallbladder; liver and plasma CA-sar-TFMA concentrations were 7.66 and 0.87 µM, respectively.

Asbt Knockout Mice

Figure 8:
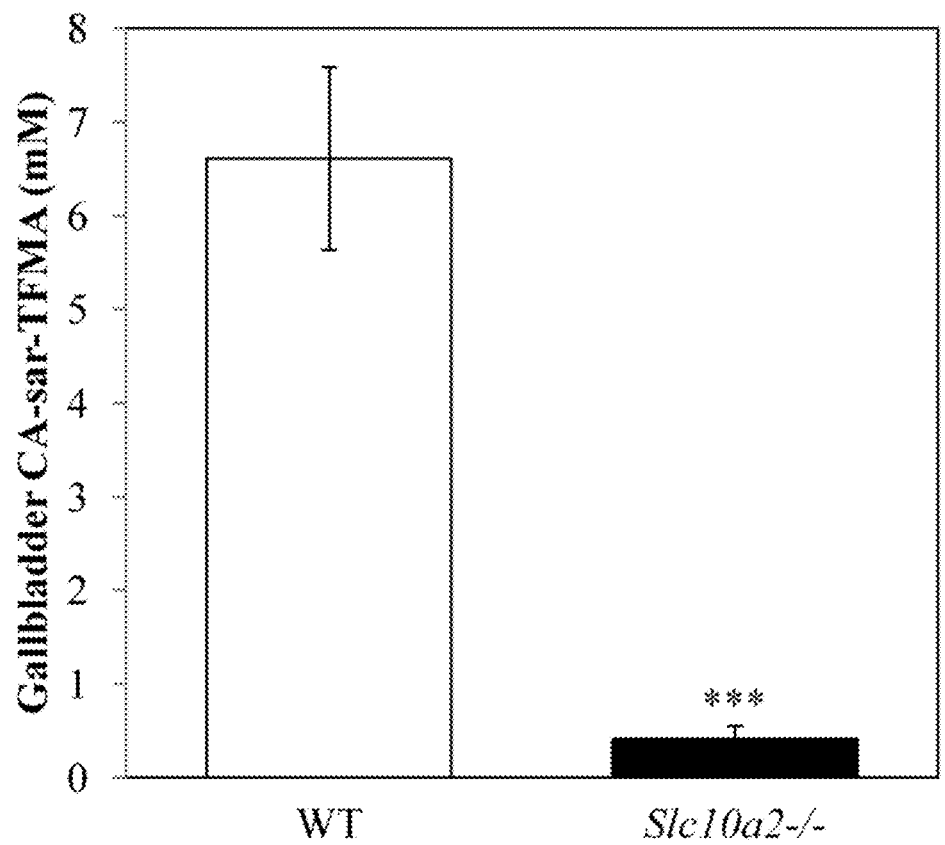
FIG. 8 shows the gallbladder concentration of CA-sar-TFMA in wild-type (WT) and knockout (Slc10A2−/) mice (n=4 each). Mice were gavaged with 150 mg/kg CA-sar-TFMA and euthanized 7 h later. LC/MS/MS analysis showed a significant difference in gallbladder concentration between the two groups (6.61±0.98 mM in WT mice vs. 0.41±0.14 mM in knockout mice, P=0.0008).

Knockout and wild-type (WT) mice (n=4) each were gavaged with 150 mg/kg CA-sar-TFMA and euthanized after 7 h. CA-sar-TFMA concentrations were determined by LC/MS/MS analysis. In FIG. 8, CA-sar-TFMA accumulated at 16.1-fold higher concentrations in WT mice gallbladders than in knockout mice gallbladders (6.61±0.98 mM vs. 0.41±0.14 mM, P=0.0008). As in the pilot disposition study, liver and plasma levels of CA-sar-TFMA were much lower than in gallbladder. Liver concentration was 4.97±1.47 µM in WT mice and 0.90±0.03 µM in knockout mice (P=0.02). Plasma concentration was 3.80±4.15 µM in WT mice and 0.22±0.09 µM in knockout mice (P=0.36). The significantly reduced levels of CA-sar-TFMA observed in Asbt knockout mice are likely due to passive absorption, in agreement with the low absorption of CA-sar previously described in studies of vascularly-perfused closed loops of rat duodenum.[34]

DISCUSSION

The objective of the present invention was to design a fluorinated bile acid resistant to bacterial enzyme deconjugation, to test its in vitro stability, transport properties, and gallbladder accumulation after oral dosing. The agent's $^{19}$F imaging characteristics were also examined, as well as its ability to differentially accumulate in the gallbladder in WT mice vs. mice with known impaired intestinal bile acid transport (Slc10A2−/− mice).

Batta et. al showed that bile acids conjugated with a tertiary amide bond at the C-24 position (i.e. sarcosine or N-methyl taurine conjugated) are resistant to deconjugation by choloylglycine hydrolase.[35] After this finding, choylylsarcosine, a conjugate of cholic acid and sarcosine, was developed as a potential conjugated bile acid replacement.[36,37] Cholylsarcosine mimics the transport of native bile acids in the enterohepatic circulation, and is not metabolized in the body by deconjugation or dehydroxylation.[38] Cholylsarcosine possesses a single negative charge in the region that promotes uptake by ASBT.[39] Based on these characteristics cholylsarcosine has been explored for use as a bile acid replacement in short bowel syndrome to enhance lipid solubilization[40] and tested as an agent to reduce intestinal bacterial overgrowth in cirrhotic rats.[41] Recently, a $^{11}$C-radiolabeled form was investigated for use in measuring the hepatic excretion of bile acids.[42]

CA-sar-TFMA was designed as a potential $^{19}$F-MRI agent that would emulate the stability of cholylsarcosine. CA-sar-TFMA is structurally similar to cholylsarcosine, but with the addition of a trifluoro-N-methyl-acetamide group. This group yields the target CA-sar-TFMA compound with three equivalent fluorine atoms, which was previously shown by the present inventors to be sufficient for $^{19}$F MRI of a fluorinated bile acid.[18,44]

CA-sar-TFMA was synthesized and tested against the sodium-dependent bile acid uptake transporters, ASBT and NTCP. CA-sar-TFMA was a potent substrate and inhibitor of both transporters. Four-hour stability testing of CA-sar-TFMA in HCl, SIF, rat plasma, rat liver s9 fraction, and choloylglycine hydrolase showed no significant compound degradation. Preliminary in vivo testing showed that an oral dose of 150 mg/kg CA-sar-TFMA accumulates in the mouse gallbladder above the minimum required for quantification by $^{19}$F MRI (6.82 mM)[18], and is present in much lower concentrations in the liver and plasma. CA-sar-TFMA was successfully imaged in the mouse gallbladder by $^{19}$F MRI, and showed a 16.1-fold difference in gallbladder accumulation in WT compared to Asbt-deficient mice. These in vivo findings suggest that the other major carriers in the enterohepatic circulation, organic solute transporters OSTα-OSTβ and bile salt export pump BSEP, also efficiently transport CA-sar-TFMA. However, minor roles cannot be excluded for other carriers such as members of the organic anion transporting peptides (OATP) family.

The in vitro transport properties of CA-sar-TFMA were characterized using cells expressing the human orthologs of NTCP and ASBT, whereas the in vivo transport was examined in mice. Studies using membrane vesicles or trans-porter-transfected cells have been used to examine the bile acid transporter properties of NTCP/Ntcp and ASBT/Asbt from individual species, though direct comparisons have not typically been performed in the same study. In general, the inter-species bile acid transport differences are small for both carriers. Human ASBT and murine Asbt have 81% identity and 88% similarity, while human NTCP and murine NTCP have 78% identity and 85% similarity (computed using the Basic Local Alignment Search Tool, NCBI-BLAST®[43]).

Compared to CA-lys-TFA, CA-sar-TFMA has similar ASBT and NTCP transport properties. CA-lys-TFA and CA-sar-TFMA are substrates of both transporters, with a higher affinity for NTCP than ASBT (CA-lys-TFA ASBT and NTCP Km values were 39.4±23.8 µM and 8.99±2.79 µM, respectively, while CA-sar-TFMA ASBT and NTCP Km values were 73.2±7.0 µM and 2.19±0.63 µM)[15]. Although CA-sar-TFMA Km and Ki values were similar for NTCP (2.19 µM vs. 2.64 µM), these values differed more than three-fold for ASBT (73.2 µM vs. 21.5 µM). It is theorized by the inventors that this Km versus Ki difference may result from binding of CA-sar-TFMA to a region of ASBT that interferes with binding of taurocholate but does not participate in uptake of CA-sar-TFMA. Such an inhibition-only binding site could account for CA-sar-TFMA being a more potent inhibitor than substrate for ASBT. Both CA-lys-TFA and CA-sar-TFMA accumulate in the mouse gallbladder at concentrations considerably greater than those in liver and plasma, and both accumulate much more in WT gallbladder compared to Asbt-deficient gallbladder. Importantly, unlike CA-lys-TFA, CA-sar-TFMA was resistant to deconjugation by choloylglycine hydrolase in vitro.

Thus, the present invention identifies CA-sar-TFMA as a novel $^{19}$F MRI probe that is available for non-invasive, in vivo diagnosis of abnormal bile acid transport.

REFERENCES

The contents of all references cited herein are incorporated by reference herein for all purposes.
1. Hofmann A F, Molino G, Milanese M, Belforter G. 1983. Description and simulation of a physiological pharmacokinetic model for the metabolism and enterohepatic circulation of bile acids in man. Cholic acid in healthy man. *J Clin Invest* 71:1003-1022.
2. Dawson, P A. 2011. Role of the intestinal bile acid transporters in bile acid and drug disposition. *Handb Exp Pharmacol* 201:169-203.
3. Wedlake L, A'Hern R, Russell D, Thomas K, Walters J R, Andreyev H J. 2009. Systematic review: the prevalence of idiopathic bile acid malabsorption (I-BAM) as diagnosed by SeHCAT scanning in patients with diarrhea-predominant irritable bowel syndrome (IBS). *Aliment Pharmacol Ther* 30:707-717.
4. Smith M J, Cherian P, Ruju G S, Dawson B F, Mahon S, Bardhan K D. 2000. Bile acid malabsorption in persistent diarrhea. *J R Coll Physicians Lond* 34:448-451.
5. Williams A J, Merrick M V, Eastwood M A. 1991. Idiopathic bile acid malabsorption—a review of clinical presentation, diagnosis, and response to treatment. *Gut* 32:1004-1006.
6. Sciarretta G, Fagioli G, Furno A, Vicini G, Cecchetti L, Grigolo B, Verri A, Malaguti P. 1987. 75Se HCAT test in the detection of bile acid malabsorption in functional diarrhea and its correlation with small bowel transit. *Gut* 28:970-975.
7. Wedlake L, Thomas K, Lalji A, Anagnostopoulos C, Andreyev H J. 2009. Effectiveness and tolerability of colesevelam hydrochloride for bile-acid malabsorption in patients with cancer: a retrospective chart review and patient questionnaire. *Clin Ther* 31:2549-2558.
8. Hofmann A F, Mangelsdorf D J, Kliewer S A. 2009. Chronic diarrhea due to excessive bile acid synthesis and not defective ileal transport: A new syndrome of defective FGF19 release. *Clin Gastroenterol Hepatol* 7:1151-1154.
9. Merrick M V, Eastwood M A, Anderson J R, Ross H M. 1982. Enterohepatic circulation in man of a gamma-emitting bile-acid conjugate, 23-Selena-25-Homotaurocholic Acid (SeHCAT). *J Nucl Med* 23:126-130.
10. Pedersen L, Arnfred T, Thaysen E H. 1973. Rapid screening of increased bile acid deconjugation and bile acid malabsorption by means of the glycine-1-(14 C) cholylglycine assay. *Scand J Gastroenterol* 8:665-672.
11. Brydon W G, Nyhlin H, Eastwood M A, Merrick M V. 1996. Serum 7 alpha-hydroxy-4-cholesten-3-one and selenohomocholyltaurine (SeHCAT) whole body retention in the assessment of bile acid induced diarrhea. *Eur J Gastroenterol Hepatol* 8:117-123.
12. Lenicek M, Duricova D, Komarek V, Gabrysova B, Lukas M, Smerhovsky Z, Vitek L. 2011. Bile acid malabsorption in inflammatory bowel disease: Assessment by serum markers. *Inflamm Bowel Dis* 17:1322-1327.
13. Khalid U, Lalji A, Stafferton R, Andreyev J. 2010. Bile acid malabsorption: a forgotten diagnosis? *Clin Med* 10:124-126.
14. Vijayvargiya P, Camilleri M, Shin A, Saenger A. 2013. Methods for diagnosis of bile acid malabsorption in clinical practice. *Clin Gastroenterol Hepatol* 11:1232-1239.
15. Vivian D, Cheng K, Khurana S, Xu S, Whiterock V, Witter D, Lentz K A, Santone K S, Raufman J-P, Polli J E. 2013. Design and characterization of a novel fluorinated magnetic resonance imaging agent for functional analysis of bile acid transporter activity. *Pharm Res* 30:1240-1251.
16. Yu J X, Kodibagkar V D, Cui W, Mason R P. 2005. $^{19}$F: A Versatile Reporter for Non-Invasive Physiology and Pharmacology Using Magnetic Resonance. *Curr Med Chem* 12:819-848.
17. Jiang Z X, Liu X, Jeong E K, Yu Y B. 2009. Symmetry-guided design and fluorous synthesis of a stable and rapidly excreted imaging tracer for ($^{19}$F) MRI. *Angew Chem Int* Ed Engl 48:4755-4758.
18. Vivian D, Cheng K, Khurana S, Xu S, Kriel E H, Dawson P A, Raufman J-P, Polli J E. 2014. In vivo performance of a novel fluorinated magnetic resonance imaging agent for functional analysis of bile acid transport. *Mol Pharm* 11, 1575-1582.
19. Dawson P A, Haywood J, Craddock A L, Wilson M, Tietjen M, Kluckman K, Maeda N, Parks J S. 2003. Targeted deletion of the ileal bile acid transporter eliminates enterohepatic cycling of bile acids in mice. *J Biol Chem* 278:33920-33927.
20. Vertzoni M, Archontaki H, Reppas C. 2008. Determination of intralumenal individual bile acids by HPLC with charged aerosol detection. *J Lipid Res* 49:2690-2695.
21. Balakrishnan A, Sussman D J, Polli J E. 2005. Development of stably transfected monolayer overexpressing the human apical sodium-dependent bile acid transporter (hASBT). Pharm Res 22:1269-1280.
22. Leonhardt M, Keiser M, Oswald S, Kuhn J, Jia J, Grube M, Kroemer H K, Siegmund W, Weitschies W. 2010. Hepatic uptake of the magnetic resonance imaging contrast agent Gd-EOB-DTPA: role of human organic anion transporters. *Drug Metab Dispos* 38:1024-8.
23. Balakrishnan A, Polli J E. 2005. Deleterious effect of high transporter expression in the estimation of transporter kinetics. *AAPS J* 7:R6224.
24. Balakrishnan A, Hussainzada N, Gonzalez P, Bermejo M, Swaan P W, Polli J E. 2007. Bias in estimation of transporter kinetic parameters from overexpression systems: Interplay of transporter expression level and substrate affinity. *J Pharmacol Exp Ther* 320:133-144.
25. Zheng X, Polli J E. 2010. Identification of Inhibitor Concentrations to Efficiently Screen and Measure Inhibition Ki Values against Solute Carrier Transporters. *Eur J Pharm Sci* 41:43-52.

26. Kolhatkar V, Polli J E. 2012. Structural requirements of bile acid transporters: C-3 and C-7 modifications of steroidal hydroxyl groups. *Eur J Pharm Sci* 46:86-99.

27. Vertzoni M, Fotaki N, Kostewicz E, Stippler E, Leuner C, Nicolaides E, Dressman J, Reppas C. 2004. Dissolution media simulating the intralumenal composition of the small intestine: physiological issues and practical aspects. *J Pharm Pharmacol* 56:453-462.

28. Huijghebaert S M, Hofmann A F. 1986. Influence of the amino acid moiety on deconjugation of bile acid amidates by cholylglycine hydrolase or human fecal cultures. *J Lipid Res* 27:742-752.

29. Committee for the Update of the Guide for the Care and Use of Laboratory Animals; National Research Council. 2011. Guide for the Care and Use of Laboratory Animals, 8th ed. Washington D.C.: National Academies Press.

30. Srinivas M, Morel P A, Ernst L A, Laidlaw D H, Ahrens E T. 2007. Fluorine-19 MRI for visualization and quantification of cell migration in a diabetes model. *Magn Reson Med* 58:725-734.

31. Li F, Zhang H, Jiang L, Zhang W, Nie J, Feng Y, Yang M, Liu M. 2007. Dynamic NMR study and theoretical calculations on the conformational exchange of valsartan and related compounds. *Magn Reson Chem* 45:929-936.

32. Zheng X, Polli J E. 2010. Identification of Inhibitor Concentrations to Efficiently Screen and Measure Inhibition Ki Values against Solute Carrier Transporters. *Eur J Pharm Sci* 41:43-52.

33. Kolhatkar V, Polli J E. 2012. Structural requirements of bile acid transporters: C-3 and C-7 modifications of steroidal hydroxyl groups. *Eur J Pharm Sci* 46:86-99.

34. Chen X, Chen F, Liu S, Glaeser H, Dawson P A, Hofmann A F, Kim R B, Shneider B L, and Pang K S. 2006. Transactivation of rat apical sodium-dependent bile acid transporter and increased bile acid transport by 1alpha,25-dihydroxyvitamin D3 via the vitamin D receptor. *Mol Pharmacol* 69:1913-1923.

35. Batta A K, Salen G, Shefer S. 1984. Substrate specificity of cholylglycine hydrolase for the hydrolysis of bile acid conjugates. *J Biol Chem* 259:15035-15039.

36. Schmassmann A, Angellotti M A, Ton-Nu H T, Schteingart C D, Marcus S N, Rossi S S, Hofmann A F. 1990. Transport, metabolism, and effect of chronic feeding of cholylsarcosine, a conjugated bile acid resistant to deconjugation and dehydroxylation. *Gastroenterology* 98:163-174.

37. Lillienau J, Schteingart C D, Hofmann A F. 1992. Physicochemical and physiological properties of cholylsarcosine. A potential replacement detergent for bile acid deficiency states in the small intestine. *J Clin Invest* 89:420-31.

38. Schmassmann A, Fehr H F, Locher J, Lillienau J, Schteingart C D, Rossi S S, Hofmann A F. 1993. Cholylsarcosine, a new bile acid analogue: metabolism and effect on biliary secretion in humans. *Gastroenterology* 104:1171-81.

39. Swaan P W, Szoka F C Jr, Oie S. Molecular modeling of the intestinal bile acid carrier: a comparative molecular field analysis study. *J Comput Aided Mol Des*. 1997; 11:581-588.

40. Heydorn S, Jeppesen P B, Mortensen P B. 1999. Bile acid replacement therapy with cholylsarcosine for short-bowel syndrome. *Scand J Gastroenterol* 34:818-823.

41. Lorenzo-Zaiga V, Bartoli R, Planas R, Hofmann A F, Vinado B, Hagey L R, Hernandez J M, Marie J, Alvarez M A, Ausina V, Gassull M A. 2003. Oral bile acids reduce bacterial overgrowth, bacterial translocation, and endotoxemia in cirrhotic rats. *Hepatology*. 37:551-557.

42. Frisch K, Jakobsen S, Sorensen M, Munk O L, Alstrup A K, Ott P, Hofmann A F, Keiding S. 2012. [N-methyl-11C]cholylsarcosine, a novel bile acid tracer for PET/CT of hepatic excretory function: radiosynthesis and proof-of-concept studies in pigs. *J Nucl Med* 53:772-778.

43. Altschul S F, Gish W, Miller W, Myers E W, Lipman D J. 1990. Basic local alignment search tool. *J Mol Biol* 215:403-410.

44. Vivian, D.; Cheng, K.; Kjurana, S., Xu, S.; Whiterock, V., Witter, D.; Lentz K.; Santone, K. S.; Raufman, J. P.; Polli, J. E.; 2013 Design and characterization of a novel fluorinated magnetic resonance imaging agent for functional analysis of bile acid transporter activity. *Pharm Res.*, 30, 1240-1251.

That which is claimed is:

1. A trifluorinated bile acid analogue compound having the following structure:

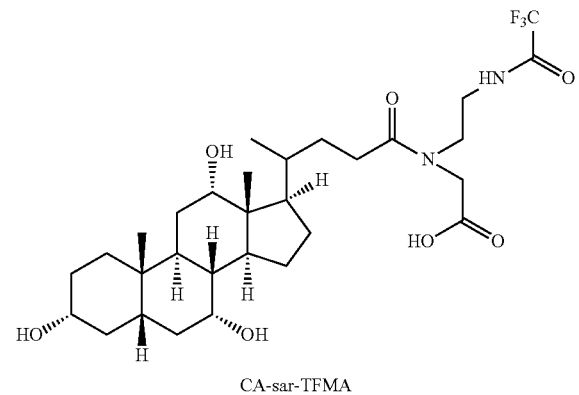

CA-sar-TFMA wherein the trifluorinated bile acid analogue compound is a $^{19}$F magnetic resonance imaging probe.

2. The trifluorinated bile acid analogue compound of claim 1, formulated for administration forms selected from tablets, capsules, powders, solutions, suspensions, dispersions or syrups.

3. The trifluorinated bile acid analogue compound of claim 2, further comprising a physiologically acceptable carrier.

4. The trifluorinated bile acid analogue compound of claim 1, wherein the compound is not susceptible to bacterial deconjugation by choloylglycine hydrolase.

5. The trifluorinated bile acid analogue compound of claim 1, wherein the compound is used to determine the mechanism underlying bile acid malabsorption.

6. A method to image gallbladder and/or gastrointestinal regions of a subject, the method comprising:

administering to a patient a CA-sar-TFMA compound having the following structure:

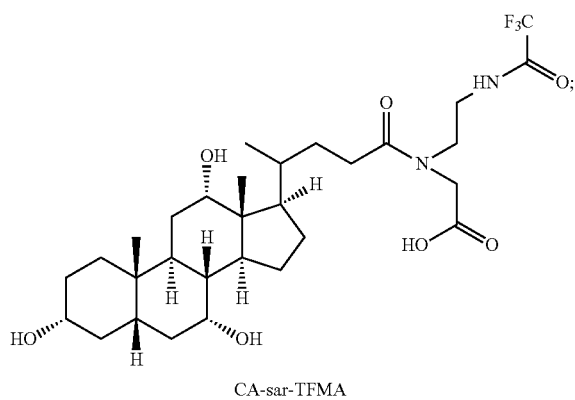

CA-sar-TFMA wherein the Ca-sar-TFMA compound is a $^{19}$F magnetic resonance imaging probe, and subjecting the patient to magnetic resonance imaging to provide magnetic resonance images of the gallbladder and/or gastrointestinal region.

7. The method of claim 6, wherein the magnetic resonance images are interpreted in comparison to baseline MRI studies to determine the mechanisms underlying bile acid malabsorption.

8. The method of claim 6, where in the administration is by oral route.

9. The method of claim 8, wherein the oral route comprising oral administration of a form selected from tablets, capsules, powders, solutions, suspensions, dispersions or syrups.

10. The method of claim 6, wherein the CA-sar-TFMA compound is combined with a physiologically acceptable carrier.

11. The method of claim 6, wherein the magnetic resonance images are used to evaluate the reabsorption of bile acids into enteroheptic system.

12. The method of claim 6, wherein the magnetic resonance images are used to monitor the progression of the disease state in a patient and/or pharmacological activity of anti-bile acid malabsorption (BAM) agents over the course of time.

13. The method of claim 6, wherein the CA-sar-TFMA compound is administered in an amount from about 5 mg/kg to 200 mg/kg.

14. A method for diagnosis of bile acid diarrhea caused by at least the failure of enterohepatic recycling of the bile acids and excess amounts of bile acid entering the colon of a subject, the method comprising:

administering to a patient CA-sar-TFMA having the following structure

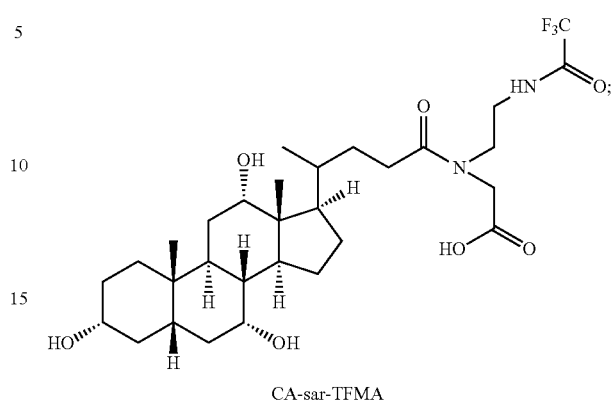

CA-sar-TFMA wherein the Ca-sar-TFMA compound is a $^{19}$F magnetic resonance imaging probe, and subjecting the patient to magnetic resonance imaging to provide magnetic resonance images.

15. The method of claim 14, wherein the magnetic resonance images are interpreted in comparison to baseline MRI studies to determine the least the failure of enterohepatic recycling of the bile acids and excess amounts of bile acid entering the colon.

16. The method of claim 14, where in the administration is by oral route.

17. The method of claim 16, wherein the oral route comprising oral administration of a form selected from tablets, capsules, powders, solutions, suspensions, dispersions or syrups.

18. The method of claim 14, wherein the CA-sar-TFMA compound is combined with a physiologically acceptable carrier.

19. The method of claim 14, wherein the magnetic resonance images are used to evaluate the reabsorption of bile acids into enteroheptic system.

20. The method of claim 14, wherein the CA-sar-TFMA compound is administered in an amount from about 5 mg/kg to 200 mg/kg.

21. The method of claim 14, wherein the magnetic resonance images are used to evaluate the activity of an anti-BAM drug.

22. A kit comprising an effective amount of the compound of claim 1 for administration into different body tissues, ducts or cavities of a subject to monitor movement of bile acids.

* * * * *